United States Patent
Sato et al.

(10) Patent No.: US 10,413,757 B2
(45) Date of Patent: Sep. 17, 2019

(54) SYSTEMS AND DEVICES FOR COUPLING ULTRASOUND ENERGY TO A BODY

(71) Applicant: Cerevast Medical, Inc., Redmond, WA (US)

(72) Inventors: Tomokazu Sato, Roanoke, VA (US); William J. Tyler, Roanoke, VA (US); Philip Lamb, San Diego, CA (US); Daniel Z. Wetmore, San Francisco, CA (US); Han-Ting Chang, Livermore, CA (US); Isy Goldwasser, Los Gatos, CA (US)

(73) Assignee: CEREVAST MEDICAL, INC., Bothell, WA (US)

( * ) Notice: Subject to any disclaimer, the term of this patent is extended or adjusted under 35 U.S.C. 154(b) by 1070 days.

(21) Appl. No.: 14/603,671

(22) Filed: Jan. 23, 2015

(65) Prior Publication Data
US 2015/0135840 A1    May 21, 2015

Related U.S. Application Data

(63) Continuation of application No. PCT/US2013/057131, filed on Aug. 28, 2013.
(Continued)

(51) Int. Cl.
*A61N 7/00* (2006.01)
*A61H 23/02* (2006.01)
(Continued)

(52) U.S. Cl.
CPC ........... *A61N 7/00* (2013.01); *A61H 23/0245* (2013.01); *G01N 29/28* (2013.01);
(Continued)

(58) Field of Classification Search
CPC ............ G01N 29/28; A61B 17/2251; A61B 2017/2253; A61B 8/00; A61B 8/4281;
(Continued)

(56) References Cited

U.S. PATENT DOCUMENTS

| | | | |
|---|---|---|---|
| 3,762,396 A | 10/1973 | Ballentine et al. | |
| 4,002,221 A | 1/1977 | buchalter | |

(Continued)

FOREIGN PATENT DOCUMENTS

| | | |
|---|---|---|
| CN | 101288600 A | 10/2008 |
| JP | S 62-35906 U | 3/1987 |

(Continued)

OTHER PUBLICATIONS

Hron, P., J. Šlechtová, K. Smetana, B. Dvořánková, and P. Lopour. "Silicone rubber-hydrogel composites as polymeric biomaterials: IX. Composites containing powdery polyacrylamide hydrogel." Biomaterials 18, No. 15 (1997): 1069-1073.*

(Continued)

*Primary Examiner* — Carolyn A Pehlke
(74) *Attorney, Agent, or Firm* — Andrew Milhollin; Yakov S. Sidorin; Quarles & Brady LLP

(57) ABSTRACT

Methods and systems for coupling ultrasound to the body, including to the head, are disclosed. The system is optionally configured to transmit ultrasound energy for transcranial ultrasound neuromodulation. Couplant assemblies are described that incorporate a semi-solid component that interfaces directly to the user's body and face of the ultrasound transducer. These couplant assemblies can be shaped, molded, or otherwise machined and, in some embodiments, contain one or more liquid, gel, or other non-solid component in an enclosed reservoir of the couplant assembly. Beneficial embodiments of ultrasound coupling assemblies described herein include those that conform to the contour of (Continued)

the user's body (e.g. the user's head for transcranial applications) and can easily be removed without leaving a messy residue. By having solid materials physically contacting the body, no residue is left that requires cleanup.

17 Claims, 15 Drawing Sheets

Related U.S. Application Data

(60) Provisional application No. 61/709,057, filed on Oct. 2, 2012, provisional application No. 61/694,714, filed on Aug. 29, 2012.

(51) Int. Cl.
   *G01N 29/28* (2006.01)
   *A61B 17/225* (2006.01)

(52) U.S. Cl.
   CPC ... *A61B 17/2251* (2013.01); *A61B 2017/2253* (2013.01); *A61H 2201/1607* (2013.01); *A61H 2201/169* (2013.01); *A61H 2205/02* (2013.01); *A61N 2007/003* (2013.01); *A61N 2007/0021* (2013.01)

(58) Field of Classification Search
   CPC ...... A61H 2201/1607; A61H 2201/169; A61H 2205/02; A61H 2205/021; A61N 7/00
   See application file for complete search history.

(56) References Cited

U.S. PATENT DOCUMENTS

| | | | |
|---|---|---|---|
| 4,059,098 A | | 11/1977 | Murdock |
| 4,309,575 A | | 1/1982 | Zweig et al. |
| 4,545,385 A | * | 10/1985 | Pirschel ............... A61B 8/0825 |
| | | | 128/915 |
| 4,556,066 A | | 12/1985 | Semrow |
| 4,646,744 A | | 3/1987 | Capel |
| 4,723,552 A | | 2/1988 | Kenyon et al. |
| 4,787,070 A | * | 11/1988 | Suzuki ............... A61B 8/4281 |
| | | | 181/400 |
| 4,886,068 A | | 12/1989 | Kaneko et al. |
| 5,127,410 A | | 7/1992 | King et al. |
| 5,394,877 A | | 3/1995 | Orr et al. |
| 5,413,550 A | | 5/1995 | Castel |
| 5,476,438 A | | 12/1995 | Edrich et al. |
| 5,494,038 A | | 2/1996 | Wang et al. |
| 5,505,205 A | | 4/1996 | Solomon et al. |
| 5,520,612 A | | 5/1996 | Winder et al. |
| 5,522,878 A | | 6/1996 | Montecalvo et al. |
| 5,540,736 A | | 7/1996 | Haimovich et al. |
| 5,558,092 A | | 9/1996 | Unger et al. |
| 5,752,924 A | | 5/1998 | Kaufman et al. |
| 5,782,767 A | | 7/1998 | Pretlow, III |
| 5,951,476 A | | 9/1999 | Beach |
| 6,039,694 A | | 3/2000 | Larson et al. |
| 6,078,838 A | | 6/2000 | Rubinstein |
| 6,182,341 B1 | | 2/2001 | Talbot et al. |
| 6,394,969 B1 | | 5/2002 | Lenhardt |
| 6,432,069 B1 | | 8/2002 | Godo et al. |
| 6,478,754 B1 | | 11/2002 | Babaev |
| 6,526,318 B1 | | 2/2003 | Ansarinia |
| 6,536,440 B1 | | 3/2003 | Dawson |
| 6,575,922 B1 | | 6/2003 | Fearnside et al. |
| 6,584,357 B1 | | 6/2003 | Dawson |
| 6,663,554 B2 | | 12/2003 | Babaev |
| 6,729,337 B2 | | 5/2004 | Dawson |
| 6,733,450 B1 | | 5/2004 | Alexandrov et al. |
| 6,735,475 B1 | | 5/2004 | Whitehurst et al. |
| 6,770,031 B2 | | 8/2004 | Hynynen et al. |
| 6,846,290 B2 | | 1/2005 | Lizzi et al. |
| 6,964,684 B2 | | 11/2005 | Ortiz et al. |
| 6,978,179 B1 | | 12/2005 | Flagg et al. |
| 7,104,947 B2 | | 9/2006 | Riehl |
| 7,108,663 B2 | | 9/2006 | Talish et al. |
| 7,190,998 B2 | | 3/2007 | Shalev et al. |
| 7,283,861 B2 | | 10/2007 | Bystritsky |
| 7,350,522 B2 | | 4/2008 | Dawson |
| 7,363,076 B2 | | 4/2008 | Yun et al. |
| 7,410,469 B1 | | 8/2008 | Talish et al. |
| 7,429,248 B1 | | 9/2008 | Winder et al. |
| 7,431,704 B2 | | 10/2008 | Babaev |
| 7,510,536 B2 | | 3/2009 | Foley et al. |
| 7,699,768 B2 | | 4/2010 | Kishawi et al. |
| 7,699,778 B2 | | 4/2010 | Adam |
| 7,713,218 B2 | | 5/2010 | Babaev et al. |
| 7,914,470 B2 | | 3/2011 | Babaev |
| 7,974,845 B2 | | 7/2011 | Spiridigliozzi et al. |
| 8,123,707 B2 | | 2/2012 | Huckle et al. |
| 8,150,537 B2 | | 4/2012 | Tanaka et al. |
| 8,190,248 B2 | | 5/2012 | Besio et al. |
| 8,235,919 B2 | | 8/2012 | Babaev |
| 8,239,030 B1 | | 8/2012 | Hagedorn et al. |
| 8,591,419 B2 | | 11/2013 | Tyler |
| 8,858,440 B2 | | 10/2014 | Tyler et al. |
| 9,042,201 B2 | | 5/2015 | Tyler et al. |
| 9,211,107 B2 | * | 12/2015 | Cox ..................... A61B 8/4281 |
| 2001/0040214 A1 | | 11/2001 | Friedman et al. |
| 2002/0042574 A1 | | 4/2002 | Manor et al. |
| 2002/0173697 A1 | | 11/2002 | Lenhardt |
| 2003/0009153 A1 | | 1/2003 | Brisken et al. |
| 2003/0032900 A1 | | 2/2003 | Ella |
| 2003/0199944 A1 | | 10/2003 | Chapin et al. |
| 2003/0204135 A1 | | 10/2003 | Bystritsky |
| 2004/0049134 A1 | | 3/2004 | Tosaya et al. |
| 2004/0059211 A1 | | 3/2004 | Suffin et al. |
| 2004/0082857 A1 | | 4/2004 | Schonenberger et al. |
| 2004/0138568 A1 | * | 7/2004 | Lo ..................... A61B 5/02438 |
| | | | 600/459 |
| 2004/0249416 A1 | | 12/2004 | Yun et al. |
| 2004/0254469 A1 | | 12/2004 | Shkarlet et al. |
| 2004/0267118 A1 | | 12/2004 | Dawson |
| 2005/0033140 A1 | | 2/2005 | De la Rosa et al. |
| 2005/0085748 A1 | | 4/2005 | Culp et al. |
| 2005/0095296 A1 | * | 5/2005 | Lowman ............... A61B 8/4281 |
| | | | 424/486 |
| 2005/0195103 A1 | | 9/2005 | Davis et al. |
| 2005/0240102 A1 | * | 10/2005 | Rachlin ................... A61B 8/10 |
| | | | 600/437 |
| 2005/0249667 A1 | | 11/2005 | Tuszynski et al. |
| 2005/0277824 A1 | | 12/2005 | Aubry et al. |
| 2006/0058678 A1 | | 3/2006 | Vitek et al. |
| 2006/0074355 A1 | | 4/2006 | Slayton et al. |
| 2006/0111754 A1 | | 5/2006 | Rezai et al. |
| 2006/0163964 A1 | | 7/2006 | Kojima et al. |
| 2006/0173321 A1 | | 8/2006 | Kubota et al. |
| 2006/0173509 A1 | | 8/2006 | Lee et al. |
| 2006/0184070 A1 | | 8/2006 | Hansmann et al. |
| 2006/0201090 A1 | | 9/2006 | Guevara et al. |
| 2006/0273509 A1 | | 12/2006 | Davis et al. |
| 2007/0016041 A1 | | 1/2007 | Nita |
| 2007/0043401 A1 | | 2/2007 | John |
| 2007/0173902 A1 | | 7/2007 | Maschino et al. |
| 2007/0179557 A1 | | 8/2007 | Maschino et al. |
| 2007/0255085 A1 | | 11/2007 | Kishawi et al. |
| 2007/0299370 A1 | | 12/2007 | Bystritsky |
| 2008/0033297 A1 | | 2/2008 | Sliwa |
| 2008/0045882 A1 | | 2/2008 | Finsterwald |
| 2008/0154332 A1 | | 6/2008 | Rezai et al. |
| 2008/0194967 A1 | | 8/2008 | Sliwa et al. |
| 2008/0200810 A1 | | 8/2008 | buchalter |
| 2008/0319376 A1 | | 12/2008 | Wilcox et al. |
| 2009/0012577 A1 | | 1/2009 | Rezai et al. |
| 2009/0024189 A1 | | 1/2009 | Lee et al. |
| 2009/0099482 A1 | | 4/2009 | Furuhata |
| 2009/0099483 A1 | | 4/2009 | Rybyanets |
| 2009/0105581 A1 | | 4/2009 | Widenhorn |
| 2009/0112133 A1 | | 4/2009 | Deisseroth et al. |
| 2009/0114849 A1 | | 5/2009 | Schneider et al. |
| 2009/0149782 A1 | | 6/2009 | Cohen |
| 2009/0221902 A1 | | 9/2009 | Myhr |

(56) References Cited

U.S. PATENT DOCUMENTS

| | | |
|---|---|---|
| 2009/0276005 A1 | 11/2009 | Pless |
| 2010/0016707 A1 | 1/2010 | Awara et al. |
| 2010/0022889 A1 | 1/2010 | Caberg et al. |
| 2010/0030299 A1 | 2/2010 | Covalin |
| 2010/0087698 A1 | 4/2010 | Hoffman |
| 2010/0125207 A1 | 5/2010 | Kim et al. |
| 2010/0125312 A1 | 5/2010 | Stevenson et al. |
| 2010/0145215 A1 | 6/2010 | Pradeep et al. |
| 2010/0234728 A1 | 9/2010 | Foley et al. |
| 2010/0324440 A1 | 12/2010 | Moore et al. |
| 2011/0009734 A1 | 1/2011 | Foley et al. |
| 2011/0040171 A1 | 2/2011 | Foley et al. |
| 2011/0040187 A1* | 2/2011 | Matsumura .......... A61B 5/6843 600/443 |
| 2011/0040190 A1 | 2/2011 | Jahnke et al. |
| 2011/0082326 A1 | 4/2011 | Mishelevich et al. |
| 2011/0092800 A1 | 4/2011 | Yoo et al. |
| 2011/0112394 A1 | 5/2011 | Mishelevich |
| 2011/0130615 A1 | 6/2011 | Mishelevich |
| 2011/0144716 A1 | 6/2011 | Bikson et al. |
| 2011/0178441 A1 | 7/2011 | Tyler |
| 2011/0178442 A1 | 7/2011 | Mishelevich |
| 2011/0190668 A1 | 8/2011 | Mishelevich |
| 2011/0196267 A1 | 8/2011 | Mishelevich |
| 2011/0208094 A1 | 8/2011 | Mishelevich |
| 2011/0213200 A1 | 9/2011 | Mishelevich |
| 2011/0270138 A1 | 11/2011 | Mishelevich |
| 2011/0288610 A1 | 11/2011 | Brocke |
| 2012/0029393 A1 | 2/2012 | Lee |
| 2012/0053391 A1 | 3/2012 | Mishelevich |
| 2012/0083719 A1 | 4/2012 | Mishelevich |
| 2012/0197163 A1 | 8/2012 | Mishelevich |
| 2012/0209346 A1 | 8/2012 | Bikson et al. |
| 2012/0245653 A1 | 9/2012 | Bikson et al. |
| 2012/0265261 A1 | 10/2012 | Bikson et al. |
| 2012/0283502 A1 | 11/2012 | Mishelevich |
| 2012/0289869 A1 | 11/2012 | Tyler |
| 2013/0066239 A1 | 3/2013 | Mishelevich |
| 2013/0066350 A1 | 3/2013 | Mishelevich |
| 2013/0079682 A1 | 3/2013 | Mishelevich |
| 2013/0144192 A1 | 6/2013 | Mishelevich |
| 2013/0178765 A1 | 7/2013 | Mishelevich |
| 2014/0094720 A1 | 4/2014 | Tyler et al. |
| 2014/0194726 A1 | 7/2014 | Mishelevich et al. |
| 2014/0211593 A1 | 7/2014 | Tyler et al. |
| 2015/0025422 A1 | 1/2015 | Tyler et al. |
| 2015/0151142 A1 | 6/2015 | Tyler et al. |
| 2015/0174418 A1 | 6/2015 | Tyler et al. |
| 2015/0343242 A1 | 12/2015 | Tyler et al. |

FOREIGN PATENT DOCUMENTS

| | | |
|---|---|---|
| JP | H 11290368 A | 10/1999 |
| JP | 2000-040191 A | 2/2000 |
| JP | 2001-327495 A | 11/2001 |
| JP | 2002-000613 A | 1/2002 |
| JP | 2006-192181 A | 7/2006 |
| JP | 2006-195872 A | 7/2006 |
| JP | 2007-517534 A | 7/2007 |
| WO | WO 94/06380 A1 | 3/1994 |
| WO | WO 98/07367 A1 | 2/1998 |
| WO | WO 2005/122933 A1 | 12/2005 |
| WO | WO 2006/026459 A2 | 3/2006 |
| WO | WO 2007/130308 A2 | 11/2007 |
| WO | WO 2007/130308 A3 | 1/2008 |
| WO | WO 2008/017998 A2 | 2/2008 |
| WO | WO 2008/089003 A2 | 7/2008 |
| WO | WO 2008/089003 A3 | 9/2008 |
| WO | WO 2009/017264 A1 | 2/2009 |
| WO | WO 2006/026459 A3 | 4/2009 |
| WO | WO 2010/009141 A1 | 1/2010 |
| WO | WO 2010/120823 A2 | 10/2010 |
| WO | WO 2011/057028 A1 | 5/2011 |
| WO | WO 2013/059833 A1 | 4/2013 |

OTHER PUBLICATIONS

Shore Durometer Conversion Chart (Polymer Properties Database, http://polymerdatabase.com/polymer%20physics/Shore%20Table.html, retrieved Jun. 29, 2018).*

Definition of Heterochromatic (https://www.collinsdictionary.com/us/dictionary/english/heterochromatic, retrieved Jun. 28, 2018).*

Polyurethane (http://www.essentialchemicalindustry.org/polymers/polyurethane.html, Apr. 24, 2017).*

Durometer Shore Hardness Scale (https://www.smooth-on.com/page/durometer-shore-hardness-scale/, Jul. 4, 2018).*

Oun, Ahmed A., and Jong-Whan Rhim. "Carrageenan-based hydrogels and films: Effect of ZnO and CuO nanoparticles on the physical, mechanical, and antimicrobial properties." Food Hydrocolloids 67 (2017): 45-53.*

Office action dated Aug. 12, 2015 for U.S. Appl. No. 14/460,007.

Notice of allowance dated Mar. 10, 2015 for U.S. Appl. No. 13/657,401.

Notice of allowance dated Mar. 31, 2015 for U.S. Appl. No. 13/657,401.

Office action dated Mar. 13, 2015 for U.S. Appl. No. 13/453,179.

Office action dated Apr. 6, 2015 for U.S. Appl. No. 14/460,007.

U.S. Appl. No. 14/501,523, filed Sep. 30, 2014, Tyler et al.

U.S. Appl. No. 14/576,588, filed Dec. 19, 2014, Tyler et al.

Additional figures for cog enhancement NPA. Jan. 1, 2013.

Arroyo, et al. Mirth, laughter and gelastic seizures. Brain. Aug. 1993;116 ( Pt 4):757-80.

Bachtold, et al. Focused ultrasound modifications of neural circuit activity in a mammalian brain. Ultrasound Med Biol. May 1998;24(4):557-65.

Baker, et al. Deep brain stimulation for obsessive-compulsive disorder: using functional magnetic resonance imaging and electrophysiological techniques: technical case report. Neurosurgery. Nov. 2007;61(5 Suppl 2):E367-8; discussion E368.

Bartsch, et al. Stimulation of the greater occipital nerve induces increased central excitability of dural afferent input. Brain. Jul. 2002;125(Pt 7):1496-509.

Boddaert, et al. Autism: functional brain mapping of exceptional calendar capacity. Br J Psychiatry. Jul. 2005;187:83-6.

Breneman, et al. Piezo- and Flexoelectric Membrane Materials Underlie Fast Biological Motors in the Ear. Mater Res Soc Symp Proc. 2009 Spring;1186E. pii: 1186-JJ06-04.

Burns, et al. Treatment of medically intractable cluster headache by occipital nerve stimulation: long-term follow-up of eight patients. Lancet. Mar. 31, 2007;369(9567):1099-106.

Bystritsky, et al. A review of low-intensity focused ultrasound pulsation. Brain Stimul. Jul. 2011;4(3):125-36. Epub Apr. 1, 2011.

Clarke, et al. Transcranial magnetic stimulation for migraine: clinical effects. J Headache Pain. Oct. 2006;7(5):341-6. Epub Oct. 25, 2006.

Clement, et al. A non-invasive method for focusing ultrasound through the human skull. Phys Med Biol. Apr. 21, 2002;47(8):1219-36.

ClinicalTrials. Deep brain stimulation (DBS) for treatment resistant bipolar disorder. Oct. 2012. www.clinicaltrials.gov. Accessed Dec. 17, 2012.

Dalecki. Mechanical bioeffects of ultrasound. Annu Rev Biomed Eng. 2004;6:229-48.

Dmochowski, et al. Optimized multi-electrode stimulation increases focality and intensity at target. J Neural Eng. Aug. 2011;8(4):046011. doi: 10.1088/1741-2560/8/4/046011. Epub Jun. 10, 2011.

European search report and opinion dated Mar. 18, 2013 for EP Application No. 10829128.7.

European search report and opinion dated Oct. 19, 2011 for EP Application No. 09798662.4.

European search report and opinion dated Dec. 8, 2014 for EP Application No. 14182336.9.

Farrell, et al. Study of the human visual cortex: direct cortical evoked potentials and stimulation. J Clin Neurophysiol. Feb. 2007;24(1):1-10.

Feurra, et al. Frequency specific modulation of human somatosensory cortex. Front Psychol. 2011;2:13. Epub Feb. 2, 2011.

(56) References Cited

OTHER PUBLICATIONS

Fleury, et al. New piezocomposite transducers for therapeutic ultrasound. 2nd International Symposium on Therapeutic Ultrasound—Seattle—Jul. 31-Aug. 2, 2002.
Gavrilov, et al. Application of focused ultrasound for the stimulation of neural structures. Ultrasound Med Biol. 1996;22(2):179-92.
Gavrilov, et al. The effect of focused ultrasound on the skin and deep nerve structures of man and animal. Prog Brain Res. 1976;43:279-92.
George, et al. Changes in mood and hormone levels after rapid-rate transcranial magnetic stimulation (rTMS) of the prefrontal cortex. J Neuropsychiatry Clin Neurosci. 1996 Spring;8(2):172-80.
George, et al. Daily repetitive transcranial magnetic stimulation (rTMS) improves mood in depression. Neuroreport. Oct. 2, 1995;6(14):1853-6.
George, et al. Vagus nerve stimulation: a new tool for brain research and therapy. Biol Psychiatry. Feb. 15, 2000;47(4):287-95.
Ghanam, et al. Vagal nerve stimulator implantation: an otolaryngologist's perspective. Otolaryngol Head Neck Surg. Jul. 2006;135(1):46-51.
Griesbauer, et al. Wave propagation in lipid monolayers. Biophys J. Nov. 18, 2009;97(10):2710-6.
Hauptman, et al. Potential surgical targets for deep brain stimulation in treatment-resistant depression. Neurosurg Focus. 2008;25(1):E3.
Heimburg. Lipid ion channels. Biophys Chem. Aug. 2010;150(1-3):2-22. Epub Mar. 11, 2010.
Hynynen, et al. 500-element ultrasound phased array system for noninvasive focal surgery of the brain: a preliminary rabbit study with ex vivo human skulls. Magn Reson Med. Jul. 2004;52(1):100-7.
Hynynen, et al. Clinical applications of focused ultrasound—the brain. Int J Hyperthermia. Mar. 2007;23(2):193-202.
Hynynen, et al. Demonstration of potential noninvasive ultrasound brain therapy through an intact skull. Ultrasound Med Biol. Feb. 1998;24(2):275-83.
International search report and written opinion dated Feb. 14, 2013 for PCT/US2012/061396.
International search report and written opinion dated Mar. 14, 2011 for PCT/US2010/055527.
International search report and written opinion dated Jul. 24, 2013 for PCT Application No. US2013/035014.
International search report and written opinion dated Sep. 10, 2009 for PCT/US2009/050560.
International search report and written opinion dated Oct. 8, 2013 for PCT Application No. US2013/047174.
International search report and written opinion dated Dec. 2, 2013 for PCT Application No. US2013/057131.
Johansen-Berg, et al. Anatomical connectivity of the subgenual cingulate region targeted with deep brain stimulation for treatment-resistant depression. Cereb Cortex. Jun. 2008;18(6):1374-83. Epub Oct. 10, 2007.
Komisaruk, et al. Brain activation during vaginocervical self-stimulation and orgasm in women with complete spinal cord injury: fMRI evidence of mediation by the vagus nerves. Brain Res. Oct. 22, 2004;1024(1-2):77-88.
Komisaruk, et al. Functional MRI of the brain during orgasm in women. Annu Rev Sex Res. 2005;16:62-86.
Latikka, et al. Conductivity of living intracranial tissues. Phys Med Biol. Jun. 2001;46(6):1611-6.
Lee, et al. Neural correlates of affective processing in response to sad and angry facial stimuli in patients with major depressive disorder. Prog Neuropsychopharmacol Biol Psychiatry. Apr. 1, 2008;32(3):778-85. Epub Dec. 23, 2007.
Lee, et al. The neural substrates of affective processing toward positive and negative affective pictures in patients with major depressive disorder. Prog Neuropsychopharmacol Biol Psychiatry. Oct. 1, 2007;31(7):1487-92. Epub Jul. 5, 2007.
Lipton, et al. Single-pulse transcranial magnetic stimulation for acute treatment of migraine with aura: a randomised, double-blind, parallel-group, sham-controlled trial. Lancet Neurology. 2010; 9(4):373-380. doi:10.1016/S1474-4422(10)70054-5.
Mayberg, et al. Deep brain stimulation for treatment-resistant depression. Neuron. Mar. 3, 2005;45(5):651-60.
Mayo Clinic staff. Bipolar disorder: treatments drugs. Mayo Clinic. Aug. 2012. www.mayoclinic.com. Accessed Dec. 17, 2012.
Meloy, et al. Neurally augmented sexual function in human females: a preliminary investigation. Neuromodulation. Jan. 2006;9(1):34-40. doi: 10.1111/j.1525-1403.2006.00040.x.
Mendelsohn, et al. Neurosurgeons' perspectives on psychosurgery and neuroenhancement: a qualitative study at one center. J Neurosurg. Dec. 2010;113(6):1212-8. doi: 10.3171/2010.5.JNS091896. Epub Jun. 4, 2010.
Menkes, et al. Right frontal lobe slow frequency repetitive transcranial magnetic stimulation (SF r-TMS) is an effective treatment for depression: a case-control pilot study of safety and efficacy. J Neurol Neurosurg Psychiatry. Jul. 1999;67(1):113-5.
Mihran, et al. Temporally-specific modification of myelinated axon excitability in vitro following a single ultrasound pulse. Ultrasound Med Biol. 1990;16(3):297-309.
Milad, et al. The role of the orbitofrontal cortex in anxiety disorders. Ann N Y Acad Sci. Dec. 2007;1121:546-61. Epub Aug. 14, 2007.
Miller, et al. Assessment tools for adult bipolar disorder. Clin Psychol (New York). Jun. 1, 2009;16(2):188-201.
Miller, et al. Enhanced artistic creativity with temporal lobe degeneration. Lancet. Dec. 21-28, 1996;348(9043):1744-5.
Morris, et al. Lipid Stress at Play: Mechanosensitivity of Voltage-Gated Channels. Current Topics in Membranes. 2007; 59:297-338.
Morris, et al. Nav channel mechanosensitivity: activation and inactivation accelerate reversibly with stretch. Biophys J. Aug. 1, 2007;93(3):822-33. Epub May 11, 2007.
Muehlberger, et al. Lasting outcome of the surgical treatment of migraine headaches—a four year follow-up. Meeting of the American Society of Plastic Surgery. Abstract #14728 Nov. 3, 2008.
Nakao, et al. Working memory dysfunction in obsessive-compulsive disorder: a neuropsychological and functional MRI study. J Psychiatr Res. May 2009;43(8):784-91. Epub Dec. 10, 2008.
Nitsche, et al. Excitability changes induced in the human motor cortex by weak transcranial direct current stimulation. J Physiol. Sep. 15, 2000;527 Pt 3:633-9.
Norton. Can ultrasound be used to stimulate nerve tissue? Biomed Eng Online. Mar. 4, 2003;2:6.
Notice of allowance dated Jul. 1, 2013 for U.S. Appl. No. 13/003,853.
Notice of allowance dated Aug. 1, 2014 for U.S. Appl. No. 14/025,586.
O'Brien. Ultrasound-biophysics mechanisms. Prog Biophys Mol Biol. Jan.-Apr. 2007;93(1-3):212-55. Epub Aug. 8, 2006.
Office action dated Jan. 31, 2013 for U.S. Appl. No. 13/200,903.
Office action dated Feb. 14, 2013 for U.S. Appl. No. 12/940,052.
Office action dated Feb. 14, 2013 for U.S. Appl. No. 13/252,054.
Office action dated Feb. 19, 2013 for U.S. Appl. No. 13/031,192.
Office action dated Feb. 26, 2013 for U.S. Appl. No. 13/007,626.
Office action dated Apr. 11, 2014 for U.S. Appl. No. 14/025,586.
Office action dated May 25, 2012 for U.S. Appl. No. 13/031,192.
Office action dated Jun. 5, 2012 for U.S. Appl. No. 13/020,016.
Office action dated Jun. 5, 2012 for U.S. Appl. No. 13/021,785.
Office action dated Jun. 6, 2012 for U.S. Appl. No. 13/252,054.
Office action dated Jun. 8, 2012 for U.S. Appl. No. 12/940,052.
Office action dated Jun. 14, 2012 for U.S. Appl. No. 13/098,473.
Office action dated Aug. 20, 2012 for U.S. Appl. No. 13/003,853.
Office action dated Sep. 27, 2012 for U.S. Appl. No. 13/007,626.
Office action dated Sep. 30, 2014 for U.S. Appl. No. 13/657,401.
Office action dated Oct. 16, 2012 for U.S. Appl. No. 13/020,016.
Office action dated Oct. 22, 2013 for U.S. Appl. No. 13/426,424.
Office action dated Oct. 22, 2013 for U.S. Appl. No. 13/551,420.
Office action dated Oct. 28, 2013 for U.S. Appl. No. 13/426,424.
Office action dated Oct. 28, 2013 for U.S. Appl. No. 13/551,420.
Office action dated Nov. 20, 2012 for U.S. Appl. No. 13/021,785.
Patoine. Deep brain stimulation for severe depression: new results suggest it works, but how? Dana Foundation. Mar. 2012. www.dana.org/media/detail.aspx?id=35782. Accessed Dec. 17, 2012.
Petrov, et al. Flexoelectric effects in model and native membranes containing ion channels. Eur Biophys J. 1993;22(4):289-300.

(56) References Cited

OTHER PUBLICATIONS

Reiman, et al. Neuroanatomical correlates of a lactate-induced anxiety attack. Arch Gen Psychiatry. Jun. 1989;46(6):493-500.
Rinaldi, et al. Modification by focused ultrasound pulses of electrically evoked responses from an in vitro hippocampal preparation. Brain Res. Aug. 30, 1991;558(1):36-42.
Sailer, et al. Effects of peripheral sensory input on cortical inhibition in humans. J Physiol. Oct. 15, 2002;544(Pt 2):617-29.
Satow, et al. Mirth and laughter arising from human temporal cortex. J Neurol Neurosurg Psychiatry. Jul. 2003;74(7):1004-5.
Schienle, et al. Symptom provocation and reduction in patients suffering from spider phobia: an fMRI study on exposure therapy. Eur Arch Psychiatry Clin Neurosci. Dec. 2007;257(8):486-93. Epub Sep. 27, 2007.
Shealy, et al. Reversible effects of ultrasound on spinal reflexes. Arch Neurol. May 1962;6:374-86.
Shirvalkar, et al. Cognitive enhancement with central thalamic electrical stimulation. Proc Natl Acad Sci U S A. Nov. 7, 2006;103(45):17007-12. Epub Oct. 25, 2006.
Snyder, et al. Concept formation: 'object' attributes dynamically inhibited from conscious awareness. J Integr Neurosci. Mar. 2004;3(1):31-46.
Snyder, et al. Savant-like skills exposed in normal people by suppressing the left fronto-temporal lobe. J Integr Neurosci. Dec. 2003;2(2):149-58.
Sperli, et al. Contralateral smile and laughter, but no mirth, induced by electrical stimulation of the cingulate cortex. Epilepsia. Feb. 2006;47(2):440-3.
Sukharev, et al. Mechanosensitive channels: multiplicity of families and gating paradigms. Sci STKE. Feb. 3, 2004;2004(219):re4.
Ter Haar. Therapeutic applications of ultrasound. Prog Biophys Mol Biol. Jan.-Apr. 2007;93(1-3):111-29. Epub Aug. 4, 2006.
Tsui, et al. In vitro effects of ultrasound with different energies on the conduction properties of neural tissue. Ultrasonics. Jun. 2005;43(7):560-5. Epub Dec. 18, 2004.
Tufail, et al. Transcranial pulsed ultrasound stimulates intact brain circuits. Neuron. Jun. 10, 2010;66(5):681-94.
Tufail, et al. Ultrasonic neuromodulation by brain stimulation with transcranial ultrasound. Nat Protoc. Sep. 1, 2011;6(9):1453-70. doi: 10.1038/nprot.2011.371.
Tyler, et al. Remote excitation of neuronal circuits using low-intensity, low-frequency ultrasound. PLoS One. 2008;3(10):e3511. Epub Oct. 29, 2008.
Velling, et al. Modulation of the functional state of the brain with the aid of focused ultrasonic action. Neurosci Behav Physiol. Sep.-Oct. 1988;18(5):369-75.
Yang, et al. Transcranial ultrasound stimulation: a possible therapeutic approach to epilepsy. Med Hypotheses. Mar. 2011;76(3):381-3. Epub Dec. 8, 2010.
Yoo, et al. Focused ultrasound modulates region-specific brain activity. Neuroimage. Jun. 1, 2011;56(3):1267-75. Epub Feb. 24, 2011.
Yoo, et al. Transcranial focused ultrasound to the thalamus alters anesthesia time in rats. Neuroreport. Oct. 26, 2011;22(15):783-7.
Yucel, et al. Anterior cingulate dysfunction: implications for psychiatric disorders? J Psychiatry Neurosci. Sep. 2003;28(5):350-4.
Zaehle, et al. Transcranial alternating current stimulation enhances individual alpha activity in human EEG. PLoS One. Nov. 1, 2010;5(11):e13766.
Zaghi, et al. Noninvasive brain stimulation with low-intensity electrical currents: putative mechanisms of action for direct and alternating current stimulation. Neuroscientist. Jun. 2010;16(3):285-307. Epub Dec. 29, 2009.
Zhao, et al. Altered default mode network activity in patient with anxiety disorders: an fMRI study. Eur J Radiol. Sep. 2007;63(3):373-8. Epub Apr. 2, 2007.
U.S. Appl. No. 14/692,326, filed Apr. 21, 2015, Tyler et al.
European search report and opinion dated Apr. 21, 2015 for EP Application No. 12841810.

\* cited by examiner

SYSTEMS AND DEVICES FOR COUPLING ULTRASOUND ENERGY TO A BODY

CROSS-REFERENCE

This application is a continuation of PCT/US2013/057131 filed on Aug. 28, 2013 which claims the benefit of priority of U.S. Provisional Patent Application No. 61/694,714 filed Aug. 29, 2012 and U.S. Provisional Patent Application No. 61/709,057 filed Oct. 2, 2012, the entire disclosures of which are incorporated herein by reference.

FIELD OF THE DISCLOSURE

Field of the Disclosure

The present disclosure relates to systems and devices for coupling ultrasound energy to the body. Embodiments include systems and devices for coupling ultrasound energy to the head, including systems configured to transmit ultrasound energy for transcranial ultrasound neuromodulation.

Background of the Disclosure

Ultrasound (hereinafter "US") has been used for many medical applications, and is generally known as cyclic sound pressure with a frequency greater than the upper limit of human hearing. An important benefit of ultrasound therapy is its non-invasive nature. US waveforms can be defined by their acoustic frequency, intensity, waveform duration, and other parameters that vary the timecourse of acoustic waves in a target tissue.

Effective coupling of ultrasound energy into the body is required for imaging and therapeutic applications. Ultrasound systems that inefficiently couple US into the body are less than ideal for several reasons including excess power requirements, heating of US components and the tissue of the subject, and distortions of US waves. Clinical and other applications of ultrasound generally use gels as a couplant from a transducer to the body. However, these gels can be less than ideal in at least some instances, including by being uncomfortable and messy, particularly when ultrasound is delivered to the head or another hairy area of the body. Another reason that ultrasound gel is less than ideal in at least some instances is that it is generally not reusable.

Systems and devices that provide efficient transmission of ultrasound energy into the head while also being comfortable and clean would be advantageous for various transcranial ultrasound applications, including transcranial ultrasound neuromodulation. Of particular use would be systems and devices for efficient transmission of ultrasound energy into the head that are reusable and/or replaceable. The present disclosure describes ultrasound coupling systems and devices that achieve the desirable features described above.

Recent research and disclosures have described the use of transcranial ultrasound neuromodulation to activate, inhibit, or modulate neuronal activity. See e.g., Bystritsky et al., 2011; Tufail et al., 2010; Tufail et al., 2011; Tyler et al., 2008; Yang et al., 2011; Yoo et al., 2011; Zaghi et al., 2010, the full disclosures of which are incorporated herein by reference. Also see e.g., U.S. Pat. No. 7,283,861 and U.S. Publication Nos. 2007/0299370 and 2011/0092800, entitled "Methods for Modifying Currents in Neuronal Circuits" by Alexander Bystritsky; U.S. Patent Application No. 2008/0045882, entitled "Biological Cell Acoustic Enhancement and Stimulation" by Finsterwald; U.S. patent application Ser. No. 13/003,853 (published as U.S. Publication No. 2011/0178441), entitled "Methods and Devices for Modulating Cellular Activity Using Ultrasound"; PCT Application No. PCT/US2010/055527 (published as PCT Publication No: WO/2011/057028), entitled "Devices and Methods for Modulating Brain Activity"; U.S. Application No. 61/550,334, entitled "Improvement of Direct Communication." Transcranial ultrasound neuromodulation is an advantageous form of brain stimulation due to its non-invasiveness, safety, focusing characteristics, and the capacity to vary transcranial ultrasound neuromodulation waveform protocols for specificity of neuromodulation.

To affect brain function transcranial ultrasound neuromodulation requires appropriate ultrasound waveform parameters, including acoustic frequencies generally less than about 10 MHz, spatial-peak temporal-average intensity generally less than about 10 W/cm$^2$, and appropriate pulsing and other waveform characteristics to ensure that heating of a targeted brain region does not exceed about 2 degrees Celsius for more than about 5 seconds. Transcranial ultrasound neuromodulation induces neuromodulation primarily through vibrational or mechanical mechanisms. Noninvasive and nondestructive transcranial ultrasound neuromodulation is in contrast to other transcranial ultrasound based techniques that use a combination of parameters to disrupt, damage, destroy, or otherwise affect neuronal cell populations so that they do not function properly and/or cause heating to damage or ablate tissue.

Effective strategies for coupling ultrasound to the body use materials with impedance values chosen to be close to the acoustic impedance of the body. Due to the large difference in speed of sound between air and tissue, an ultrasound waveform can be distorted by one or more of refraction, reflection, absorption, or other distortion if effective acoustic coupling is not achieved. Effective ultrasound couplants are designed to minimize air-tissue boundaries.

The prior methods and apparatus for coupling can be messy and less than ideally suited for ongoing use by a subject. In prior diagnostic and therapeutic ultrasound practice, an ultrasound gel is spread on the skin to couple ultrasound energy into and out from the body. Formulations include aqueous solutions containing thickeners consisting of alkali metal salts of long chain ionic organic polymers (Buchalter, U.S. Pat. No. 4,002,221 titled "Method of transmitting ultrasonic impulses to surface using transducer coupling agent") or aqueous solutions of a hydrophilic polymer, notably polyvinylpyrrolidone (Joseph Godo et. al., U.S. Pat. No. 6,432,069 titled "Coupling medium for high-power ultrasound"). Various delivery systems for these liquid solutions have also been proposed, including one for ultrasound imaging wherein a porous membrane and an ultrasound probe cooperate to define a chamber which contains a liquid acoustical couplant. When pressure is applied to the liquid acoustical couplant it passes through the porous membrane (Wang et. al., U.S. Pat. No. 5,494,038 titled "Apparatus for ultrasound testing")

Ultrasound gel can be uncomfortable, sticky, and difficult to clean up. Cleanup in hairier areas of the body such as the head can be more difficult, in part due to large quantities of gel that may be required to ensure efficient coupling. Due to the inconvenience, discomfort, and messiness of ultrasound gels, alternative systems and devices for coupling ultrasound energy transcranially would be advantageous.

Systems for ultrasound coupling that do not require cleaning after use have been disclosed, including coupling pads and other enclosures, as well as couplants made of very hard materials. A selection of this prior art is discussed briefly below.

Enclosed assemblies that contain a liquid or gel for coupling ultrasound have been disclosed. Jahnke et al.

disclose an ultrasound imaging system that incorporates a container for holding ultrasound gel (U.S. patent application Ser. No. 12/858,242 titled "Disposable Acoustic Coupling Medium Container"). Larson et al. disclose a flexible, elastic sheath that conforms to the housing of an ultrasound transducer and contains ultrasound gel (U.S. Pat. No. 6,039,694 titled "Coupling sheath for ultrasound transducers"). Murdock discloses a fluid medium contained in a rigid container for coupling ultrasound into a specimen (U.S. Pat. No. 4,059,098 titled "Flexible ultrasound coupling system."). Previously disclosed enclosed assemblies that contain a liquid or gel for coupling ultrasound are lacking in at least some respects, for instance due to the complexity of a system requiring manufacturing an enclosure and filling it with liquid or gel ultrasound couplant.

Several disclosures have described adhesive 'patch' style ultrasound coupling assemblies. Semrow discloses a coupling pad that contains acoustical gel (U.S. Pat. No. 4,556,066 titled "Ultrasound acoustical coupling pad"). Buchalter discloses a disposable ultrasound coupling pad that adheres to a patient's skin (U.S. patent application Ser. No. 11/675,977 titled "Ultrasound coupling device"). Commercial products are also available with similar feature such as a disposable, single-use product for use in neonatal transcranial ultrasound (e.g. Fontanelle scanning pad). Pretlow discloses an ultrasound coupling pad assembly that incorporates a support pad that is configured so that the coupling unit adheres more strongly to the transducer than the body (U.S. Pat. No. 5,782,767 titled "Coupling pad for use with medical ultrasound devices"). Previously disclosed adhesive 'patch' style ultrasound coupling assemblies are lacking in at least some respects, for instance due to the difficulty of adhering a coupling pad to portions of the body covered with hair. Also, disposable systems are not designed to be reused, adding cost and complexity to a US coupling system.

Solomon et al. disclose a "solid, flexible, ultrasonic biomedical couplant hydrogel in sheet form that holds its form . . . when placed on the body" (U.S. Pat. No. 5,522,878 titled "Solid multipurpose ultrasonic biomedical couplant gel in sheet form and method"). Solomon et al. also disclose polymeric compounds designed to be very rigid (Shore D durometer greater than 60 D) and to have a sound speed between 1450 meters/second and 1700 meters/second (U.S. Pat. No. 5,505,205 titled "Interface element for medical ultrasound transducer"). These couplants are lacking because they are rigid and do not conform to the head for efficient ultrasound transmission.

Reusable assemblies for coupling ultrasound energy to the head for transcranial ultrasound neuromodulation that do not require cleaning and conform to the shape of the head would be advantageous but have not been previously disclosed. Systems or assemblies that are easily replaceable by a user would be advantageous but have also not been described.

Several patents include disclosures that employ silicone as a component in an ultrasound coupling system. None of these disclosures identifies a silicone component as a couplant that directly contacts a subject while efficiently transmitting ultrasound energy into the body as shown in the disclosure herein described.

Silicone oil can be used as a low viscosity couplant for ultrasound (e.g. U.S. Pat. No. 4,886,068 to Kaneko et al. titled "Ultrasonic coupling agent"). However, silicone oil can require clean up and can be somewhat messy to use, for example with the user's hair, in at least some instances.

Talbot et al. (U.S. Pat. No. 6,182,341 titled "Method of manufacturing an improved coupling of acoustic window and les for medical ultrasound transducers") describe a method for coupling a radiofrequency (RF) shield to an acoustic window for ultrasound for reducing RF interference in a hospital environment (e.g. for phased array ultrasound systems). In some embodiments described by Talbot et al., RTV silicone is part of an RF shield. However, the silicone does not contact the subject and does not transmit ultrasound into the body.

Orr et al. (U.S. Pat. No. 5,394,877 titled "Ultrasound medical diagnostic device having a coupling medium providing self-adherence to a patient") propose silicone rubber, polyvinyl chloride, and polyurethane as suitable materials for a support element for an ultrasound couplant assembly but do not propose these materials to be used for transmission of ultrasound energy or coupling ultrasound energy directly to the body of a subject.

Fearnside and Kyle (U.S. Pat. No. 6,575,922 titled "Ultrasound signal and temperature monitoring during sonothrombolysis therapy") describe systems to treat a patient with a thrombolytic occlusion by using ultrasound for thrombolysis to clear the occlusion. The disclosure shows how a hydrophone embedded in a couplant can provide real-time feedback to control heating, and states that the coupling material may comprise a silicone material with a "thin layer of glycerine on either side thereof". Inventors state that the glycerine layer is necessary to provide sufficient coupling and do not suggest the use of silicone alone for ultrasound coupling ultrasound energy directly to the body of a subject.

SUMMARY OF THE DISCLOSURE

The present disclosure discloses systems and devices for coupling ultrasound to the body. In many advantageous embodiments, ultrasound energy is coupled to the head. In further advantageous embodiments, the system is configured to transmit ultrasound energy for transcranial ultrasound neuromodulation.

In many embodiments, systems and methods for coupling ultrasound directly to the body (including the head) of a subject are provided. In many embodiments a couplant assembly comprises a semi-solid coupling component that interfaces directly to the user's body and face of the ultrasound transducer. In many embodiments, the semi-solid coupling component comprises a material having an internal adhesion strength greater than an adhesive strength of the surface coupled to the skin or hair, such that the semi-solid coupling component can be removed from skin or hair without leaving substantial amounts of residue on the skin or hair. The couplant assembly has the advantage of providing ultrasound coupling similar to an ultrasound gel and providing for removal of the assembly without leaving a substantial amount of residue when the couplant assembly has been removed subsequent to treatment. The couplant assembly can be shaped, molded, or otherwise machined in one or more of many ways, and, in many embodiments, contains one or more liquid, gel, or other non-solid component enclosed in a reservoir of the couplant assembly. The reservoir may comprise a sealed container to inhibit leakage of the contents of the reservoir when coupled to the subject to transmit ultrasound.

The ultrasound coupling assembly can conform to the contour of the user's body (e.g. the user's head for transcranial applications) and can easily be removed without leaving a substantial residue. By having solid non-viscous materials physically contacting the body, no substantial residue remains when the coupling assembly has been removed, such that clean up may not be required in many embodiments.

In many embodiments, a couplant assembly comprises a support component and a coupling component. The support component is configured to hold one or more of water, gel, oil, or another liquid material in a reservoir. In preparation for ultrasound coupling to a portion of the body, the water, gel, oil, or other suitable couplant liquid material is released through a permeable, semi-permeable, or porous membrane to couple the ultrasound energy between the couplant and portion of the body such as the head. In many embodiments, a small amount of water, gel, oil, or other suitable couplant liquid material is sufficient for coupling, as the couplant is positioned directly against the body (e.g. the head) before or immediately after the couplant material held in the reservoir is released. In various embodiments of the disclosure, one or more systems for releasing the couplant material from the reservoir can be achieved by exerting pressure manually, by a mechanical system controlled by a switch or other user interface, or another suitable system for releasing couplant material.

The embodiments disclosed herein can be used in one or more of many ways and may comprise couplant assemblies for ultrasound imaging and therapy, including transcranial ultrasound neuromodulation, and efficiently transmit ultrasound energy to the body with minimal distortion, adhere or conform to the portion of the body to which they are attached or held in place, and require little or no cleanup after use. Couplant assemblies for ultrasound imaging and therapy directed to the head, including transcranial ultrasound neuromodulation, in accordance with embodiments disclosed herein efficiently transmit ultrasound energy transcranially with minimal distortion, adhere or conform to the head, and require little or no cleanup on the skin or hair after use. In some embodiments, the couplant assembly comprises non-solid silicone and at least one other non-solid material. In additional embodiments, the couplant assembly further comprises a stiffener made of a material stiffer than the ultrasound couplant material to add stiffness and rigidity that imparts improved mechanical stability to the couplant assembly. The stiffening component supports the components and coupling component and may not form the primary contact between the couplant assembly and the subject's body.

An aspect of the disclosure provides a system for coupling ultrasound energy to a subject. The system comprises a couplant assembly to couple ultrasound energy from at least one ultrasound transducer to the subject. The couplant assembly may be configured in many ways according to many embodiments.

In many embodiments, the couplant assembly may comprise at least one conformable solid material in physical contact with the at least one transducer. For example, the couplant assembly may comprise a conformable couplant material having a Shore D durometer hardness value of less than 60 D such that an outer surface of the couplant material can deflect at least partially in response to a skin or hair of the user when placed in order to couple the at least one ultrasound transducer to the user. The solid couplant material may be measured on the Shore A or Shore OO durometer hard scale or on the Shore OOO durometer hard scale. The solid couplant material may comprise a gel, a silicone, or one or more stiffening assembly components made of a harder material than the couplant. The couplant assembly may comprise at least one liquid or gel material contained within the conformable solid material. In some embodiments, the couplant assembly may comprise a couplant structure which may comprise a plurality of components at least one of which comprises the conformable solid material to interface directly with the at least one transducer and the body of the subject, and the couplant structure may comprise a chamber to contain the at least one liquid or gel material within the coupling structure.

In many embodiments, the coupling assembly is configured to couple to the at least one transducer and the subject in order to transmit ultrasound energy with low transmission loss and low impedance mismatch between the at least one transducer and the body of the subject.

In many embodiments, the couplant assembly is configured to contact directly the head of a subject to deliver ultrasound energy transcranially. And, the couplant assembly may be configured to induce neuromodulation via transcranial ultrasound neuromodulation.

In many embodiments, the couplant assembly comprises a deformable coupling structure in order to deform and fits the contour of the head of the subject when placed.

In many embodiments, the couplant assembly is configured to be reusable.

In many embodiments, the couplant assembly comprises a housing to contain one or more structures of the couplant assembly. In some embodiments, the housing holds the couplant assembly in contact with the at least one transducer. The housing may hold the coupling assembly in contact with the at least one transducer and comprises a retaining ring. In some embodiments, the housing is configured to couple to the at least one transducer and hold the at least one transducer when the coupling assembly is placed on the subject and removed from the subject. The coupling assembly may be configured to be removed from the at least one transducer and replaced with a second coupling assembly by the user.

In many embodiments, the system further comprises a mold for creating a shaped couplant and the coupling assembly comprises the mold and the shaped couplant.

In many embodiments, the couplant assembly is configured to couple ultrasound energy to target a peripheral nerve or vagal nerve of a subject.

In many embodiments, the couplant assembly is configured to require no cleaning of the user's scalp, skin, or hair after use.

In many embodiments, the couplant assembly comprises of at least one stiffer material held in contact with the at least one softer material to provide rigidity to the couplant assembly.

In many embodiments, one or more components of the couplant assembly are heterochromatic.

In many embodiments, the couplant assembly comprises a gel composed of physically crosslinked polymers, chemically crosslinked polymers, or the combination thereof. The gel may comprise small molecules.

In many embodiments, the couplant assembly comprises a gel prepared from naturally occurring polymers. The naturally occurring polymer may comprise one or more of collagen, gelatin, hyaluronic acid, fibrin, alginate, agarose, or chitosan. In some embodiments, the naturally occurring polymer has been formed and shaped by addition of crosslinkers to add structural stiffness.

In many embodiments, the couplant assembly comprises a gel prepared from synthetic monomers. The synthetic monomers may comprise one or more of mono-, di-, tri- or multi-functional acrylates, methacrylates, vinyls, amines, alcohol, carboxylic acids, epoxides, anhydrides, or isocyantes.

In many embodiments, the couplant assembly comprises a gel prepared from synthetic polymers. The synthetic polymers may comprise one or more of homo- or co-polymers of acids, amides, alcohols, PEGs, or amine.

Another aspect of the disclosure provides a method comprising providing a couplant assembly according to any of the many embodiments disclosed herein. The method may further comprise providing the couplant assembly according to any of the many embodiments disclosed herein.

BRIEF DESCRIPTION OF THE DRAWINGS

Embodiments of the present disclosure have other advantages and features which will be more readily apparent from the following detailed description of the disclosure and the appended claims, when taken in conjunction with the accompanying drawings, in which:

DETAILED DESCRIPTION OF THE DISCLOSURE

Figure 1:
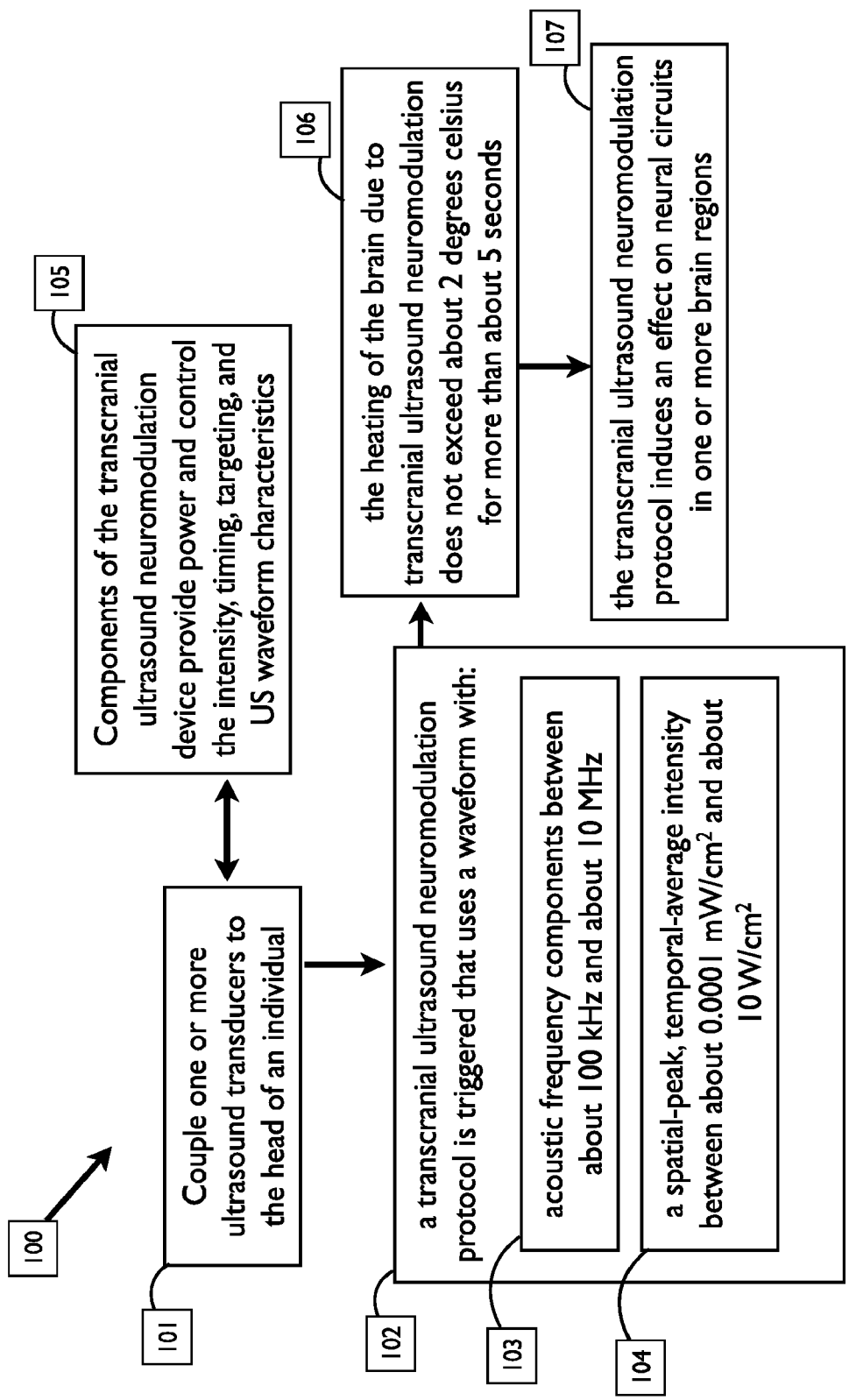
FIG. 1 shows a transcranial ultrasound neuromodulation delivery framework, in accordance with embodiments.

In this disclosure, couplant assemblies are described for transmitting ultrasound energy from at least one ultrasound transducer directly to the body of a subject. Advantageous materials include those that require minimal cleanup, that conform to the body or head of a subject, that transmit ultrasound with low transmission loss, and retain their shape during and/or between uses. Particularly advantageous embodiments are reusable.

Described herein are systems and methods for coupling ultrasound directly to the body (including the head) of a subject with an assembly that is composed of or incorporates a component that interfaces directly to the user's body and can be a shaped, molded, or otherwise machined or manufactured silicone piece. As described below, we have shown efficient transmission of ultrasound energy through shaped silicone couplants, providing an advantageous new system for coupling ultrasound energy to the human body with qualities that may include comfort, reusability, cleanliness, and ease of use (including autonomous use) without requiring an ultrasound technician.

As used herein, a framework encompasses one or more of a system, a method, and combinations thereof.

As used herein, like numerals denote like structure.

As used herein semi-solid coupling component comprises a material having an internal adhesion strength greater than an external adhesive strength of the surface coupled to the skin or hair, such that the semi-solid coupling component can be removed from skin or hair without leaving substantial amounts of residue on the skin or hair. The semi-solid coupling element may comprise a material such as a soft cured silicone or gel, for example, such that the coupling component sticks to itself more than it sticks to the skin or hair.

Couplant assemblies for ultrasound imaging and therapy, including transcranial ultrasound neuromodulation, described herein efficiently transmit ultrasound energy to the body with minimal distortion, adhere or conform to the portion of the body to which they are attached or held in place, and require minimal cleanup after use. Couplant assemblies for ultrasound imaging and therapy directed to the head, including transcranial ultrasound neuromodulation, described herein efficiently transmit ultrasound energy transcranially with minimal distortion, adhere or conform to the head, and require minimal cleanup on the skin or hair after use. In some embodiments, the couplant assembly is comprised of silicone. In some embodiments, the couplant assembly further comprises at least one other non-solid material. In other embodiments, the couplant assembly further comprises a stiffener made of harder material than the ultrasound couplant material and imparts improved mechanical stability to the couplant assembly but does not form the primary contact between the couplant assembly and the subject's body.

High viscosity, elastic, or solid silicone materials that can be molded or machined and retain their shape can be used for coupling ultrasound directly to the body of a subject and can be advantageous in at least some instances in accordance with embodiments as described herein.

In some embodiments of the disclosure, the couplant assembly adheres or conforms to the head sufficiently to transmit ultrasound energy for transcranial ultrasound neuromodulation while also having the property of being easily removed from the head by twisting or pulling, or by the application of water or another suitable liquid that does not leave a residue.

In some embodiments of the disclosure, the assembly is reusable and/or replaceable. In some embodiments of the disclosure, one or more additional components of the couplant assembly connect the couplant assembly to one or more transducers or transducer packaging components (e.g. plastic, metal, or other material that encloses the one or more ultrasound transducer and related components). In some embodiments of the disclosure, the one or more components that couple the couplant assembly to a transducer or transducer packaging component are configured to be removed by the user. Couplant assemblies may occasionally require replacement as advantageous properties degrade due to use and wear, so the removable couplant assembly permits replacement with a new couplant assembly.

In some embodiments of the disclosure, one or more components of the couplant assembly are doped with one or more heterochromatic materials so that the optical properties of the couplant assembly change when ultrasound transmission is in progress. A heterochromatic couplant assembly is advantageous for safety, feedback to the user about device function, and pleasurability of the transcranial ultrasound neuromodulation session for the user or others.

Silicone is a particularly advantageous couplant material for embodiments of this disclosure. Silicones are polymers that include silicon together with carbon, hydrogen, oxygen, and sometimes other chemical elements. Some common forms include silicone oil, silicone grease, silicone rubber, and silicone resin. Silicone gels having a range of elasticity and hardness (durometer) properties and can be purchased from companies such as Silicone Solutions (Twinsburg, Ohio). Effective materials, systems, devices, or assemblies for coupling ultrasound energy to the head of a subject during a transcranial ultrasound neuromodulation protocol would be beneficial.

Transcranial Ultrasound Neuromodulation

Transcranial ultrasound neuromodulation is a technique for modulating brain circuit activity via patterned, local vibration of brain tissue using ultrasound (US) having an acoustic frequency greater than about 100 kHz and less than about 10 MHz. In many embodiments, ultrasound energy in a transcranial ultrasound neuromodulation waveform provides ultrasound energy within a range of acoustic frequencies. In many embodiments, the transcranial ultrasound neuromodulation transmits mechanical energy through the skull to the targeted region in the brain without causing significant thermal or mechanical damage and induces neuromodulation. In many embodiments, transcranial ultrasound neuromodulation employs low intensity ultrasound such that the spatial-peak, temporal-average intensity ($I_{spta}$) of the transcranial ultrasound neuromodulation protocol provides less than about 10 W/cm2 (preferably less than about 1 W/cm$^2$) in the targeted brain tissue. The acoustic intensity measure Ispta can be calculated according to established techniques that relate to the ultrasound acoustic pressure and other transcranial ultrasound neuromodulation protocol characteristics such as the temporal average power during the transcranial ultrasound neuromodulation waveform duration. US may be delivered as short-lived continuous waves less than about 5 seconds, in a pulsed manner, or in the form of an ultrasound waveform of arbitrary complexity during transcranial ultrasound neuromodulation protocols such that diverse patterns of neuromodulation can be delivered. For modulating the activity of brain circuits through localized tissue vibration, transcranial ultrasound neuromodulation protocols may utilize US waveforms of any type known in the art. These include amplitude modulated waveforms, tone-bursts, pulsed waveforms, continuous waveforms, and other waveform patterns as described herein, for example.

FIG. 1 shows a method 100 for transcranial ultrasound neuromodulation delivery in accordance with many embodiments. In the method 100, transcranial ultrasound neuromodulation is used to induce neuromodulation in a subject whereby:

One or more transcranial ultrasound neuromodulation ultrasound transducers are coupled to the head of an individual human or animal (the "subject", "user", or "recipient") in a step 101;

1) Components of the transcranial ultrasound neuromodulation device are provided to be near or wearably attached to the recipient in order to provide power and control the intensity, timing, targeting, and waveform characteristics of the transmitted acoustic waves in a step 105;

2) a transcranial ultrasound neuromodulation protocol is triggered that uses a waveform in a step 102 that:

a. is provided with an acoustic frequency between about 100 kHz and about 10 MHz in a step 103; and b. is provided with a spatial-peak, temporal-average intensity between about 0.0001 mW/cm$^2$ and about 10 W/cm$^2$ in a step 104; and c. is provided with properties in a step 106 such that the waveform does not induce heating of the brain due to transcranial ultrasound neuromodulation that exceeds about 2 degrees Celsius for more than about 5 seconds; and 3) the transcranial ultrasound neuromodulation protocol induces an effect on neural circuits in one or more brain regions in a step 107.

US can cause the local vibration of particles, leading to both mechanical and thermal effects. In some embodiments, transcranial ultrasound neuromodulation brain stimulation protocols modulate neuronal activity primarily through mechanical means. In some embodiments for transcranial ultrasound neuromodulation, a single ultrasound pulse is delivered that may be referred to as a continuous wave (CW) pulse by one skilled in the art and extends in time for about longer than 10 ms, about longer than 100 ms, about longer than 1 second, or any length of time up to and including 5 seconds. Complex transcranial ultrasound neuromodulation waveforms, including transcranial ultrasound neuromodulation waveforms generated by hybridization, convolution, addition, subtraction, phase shifting, concatenation, and joining with an overlap for a portion of each of the waveforms for two or more transcranial ultrasound neuromodulation waveforms or transcranial ultrasound neuromodulation waveform components, as well as modulation or ramping of the intensity of all or a portion of the waveform, or modulation or ramping of any other parameter used to define an ultrasound waveform, may be advantageous for transcranial ultrasound neuromodulation in some embodiments.

Appropriate transcranial ultrasound neuromodulation protocols can be advantageous for mitigating or eliminating tissue damage while simultaneously modulating neuronal activity primarily through mechanical means in at least some embodiments. For example, low temporal average intensity can be achieved by reducing the acoustic power of the ultrasound waves or by varying one or more transcranial ultrasound neuromodulation parameters to decrease the effective duty cycle—the proportion of time during a transcranial ultrasound neuromodulation waveform that ultrasound is delivered. Reduced duty cycles can be achieved by decreasing one or more transcranial ultrasound neuromodulation parameters chosen from pulse length, cycles per pulse, pulse repetition frequency, or other waveform parameters. Low temporal average intensity can be achieved by varying one or more ultrasound parameters during a transcranial ultrasound neuromodulation protocol. For instance, the acoustic power may be decreased during a portion of a transcranial ultrasound neuromodulation protocol. Alternatively, the pulse repetition frequency can be decreased during a transcranial ultrasound neuromodulation protocol.

In other embodiments, complex ultrasound waveforms can be generated that are effective for inducing neuromodulation and maintain an appropriately low temporal average intensity.

The major advantages of transcranial ultrasound neuromodulation for brain stimulation are that it offers a mesoscopic spatial resolution of a few cubic millimeters and the ability to penetrate beyond the brain surface to the brain's deepest structures (in contrast to transcranial magnetic stimulation) while remaining completely non-invasive (in contrast to using electrodes for deep-brain stimulation). Transcranial ultrasound neuromodulation has beneficial advantages over other forms of non-invasive neuromodulation that include focusing, targeting tissues at depth, and painless stimulation procedures.

Effective delivery of ultrasound energy to the brain requires efficient, low attenuation coupling of ultrasound through the hair, skin, skill, and dura into the brain. In some embodiments described herein, devices, systems, and assemblies for coupling ultrasound energy to the head are used for transcranial ultrasound neuromodulation. In various embodiments of the disclosure, advantageous features of the couplant assembly include:

(1) Maintenance of thermal integrity: the structural and acoustic properties of the couplant materials should be stable under circumstances when the temperature of the couplant assembly rises due to device function.

(2) Maintenance of structural integrity: the size and shape of the one or more assembly components that couple ultrasound energy from the transducer to the head need to be maintained during use and re-use.

(3) Reusability: many existing methods for ultrasound coupling, including ultrasound gel and disposable ultrasound coupling pads, are not reusable. For repeated transcranial ultrasound neuromodulation protocols, a reusable couplant assembly would be advantageous. Reusability also offers the possibility of reduced cost and reduced waste. In some embodiments of the disclosure, one or more components of the couplant assembly are configured to adhere and/or conform to the head when placed in physical contact with it, yet maintain the ability to be removed by force and/or application of a small amount of water or other suitable liquid that does not leave a residue on the subject. Moreover, to be reusable, the couplant assembly maintains acoustic, structural, adherence, and conformity properties with re-use. In various embodiments of the disclosure, the couplant assembly is configured to be re-used for a number of transcranial ultrasound neuromodulation sessions chosen from the list of: once, twice, 3 times, 4 times, 5 times, more than 5 times, more than 10 times, more than 25 times, more than 50 times, more than 100 times, more than 500 times, more than 1000 times, or more than 10,000 times.

(4) Minimal cleaning: In core embodiments of the disclosure, a coupling assembly requires minimal cleanup after a transcranial ultrasound neuromodulation session. Reduced need for cleanup requires that little residue, gel, or other material remain on the head or in the hair of a user. In some embodiments of the disclosure, water or another suitable liquid is used to quickly release the couplant from the head without requiring additional cleaning. In some embodiments, minimal cleaning after removal of the couplant during a transcranial ultrasound neuromodulation session means that no soap is required for cleaning. In other embodiments, no alcohol is required for cleaning. In yet other embodiments, no cleaning wipes, tissues, or other cleaning products are required for cleaning after a transcranial ultrasound neuromodulation session.

Couplant assemblies as described herein have at least one component that directly couples the one or more ultrasound transducers with the user's head and is characterized by low transmission loss into the body. Materials having a speed of sound between about 1450 meters/second to 1700 meters/second are advantageous. This range of speeds of sound is similar to the speed of sound in the body and assures efficient ultrasound transmission.

In exemplary embodiments of the disclosure, a system for coupling ultrasound energy to the body of a subject comprises at least one semi-solid solid material in physical contact with the at least one transducer and the body of a subject and having a Shore D durometer hardness value of less than 60 D. In some embodiments, the solid couplant material is softer and its hardness is measured on the Shore A or Shore OO durometer hard scale. In other embodiments, the solid couplant material is measured on the Shore A, Shore OO, or Shore OOO durometer hard scale.

Advantageous systems are configured to transmit ultrasound energy with low transmission loss and low impedance mismatch between the at least one transducer and the body of the subject. In core embodiments, the couplant is in direct contact with the head of a subject to deliver ultrasound energy transcranially. In some embodiments, the couplant is deformable and fits the contour of the head of a subject. The couplant may be made of a gel such as silicone and in some embodiments is configured to be reusable.

In some embodiments, the couplant further comprises one or more stiffening assembly components made of a harder material than the couplant. In some embodiments, the couplant further comprising a housing for the couplant assembly. The housing can serve to hold the couplant assembly in contact with the transducer. In some embodiments the system for holding the coupling assembly in contact with the transducer is a retaining ring. The housing may also hold the transducer.

Features and components that allow a user to remove and/or replace a couplant or other component of the transducer assembly are advantageous. To create the couplant with an appropriate shape, a mold can be used. The mold can be removed after the couplant has hardened.

Embodiments that couple ultrasound energy to the head are particularly advantageous for targeting the brain or other tissue transcranially. Couplant systems that couple ultrasound energy to the head are beneficial for inducing neuromodulation via transcranial ultrasound neuromodulation, ultrasound imaging, transcranial Doppler imaging, and other diagnostic and therapeutic applications of transcranial ultrasound.

In other embodiments, a system incorporating a couplant assembly targeted to the head is configured to transmit high intensity ultrasound in order to ablate, heat, or mechanically disrupt brain tissue. In some embodiments configured for transcranial ablation, heating, or mechanical disruption of brain tissue, the couplant assembly has a liquid or gel reservoir.

In other embodiments, a couplant assembly is used to couple ultrasound energy to the spinal cord of a subject. Couplant systems that couple ultrasound energy to the spinal cord are beneficial for inducing neuromodulation via transcranial ultrasound neuromodulation, ultrasound imaging, and other diagnostic and therapeutic applications of ultrasound. In other embodiments, a system incorporating a couplant assembly targeted to the spinal cord is configured to transmit high intensity ultrasound in order to ablate, heat, or mechanically disrupt neural tissue. In some embodiments targeting the spinal cord, the couplant assembly has a liquid or gel reservoir.

In other embodiments, a couplant assembly is used to couple ultrasound energy to a portion of the body for targeting a peripheral nerve or vagal nerve. Couplant systems that couple ultrasound energy to be delivered to a peripheral nerve or vagal nerve are beneficial for inducing neuromodulation via transcranial ultrasound neuromodulation, ultrasound imaging, and other diagnostic and therapeutic applications of ultrasound. In other embodiments, a system incorporating a couplant assembly targeted to a peripheral nerve or vagal nerve is configured to transmit high intensity ultrasound in order to ablate, heat, or mechanically disrupt neural tissue. In some embodiments targeting a peripheral nerve or vagal nerve, the couplant assembly has a liquid or gel reservoir.

Figure 2:
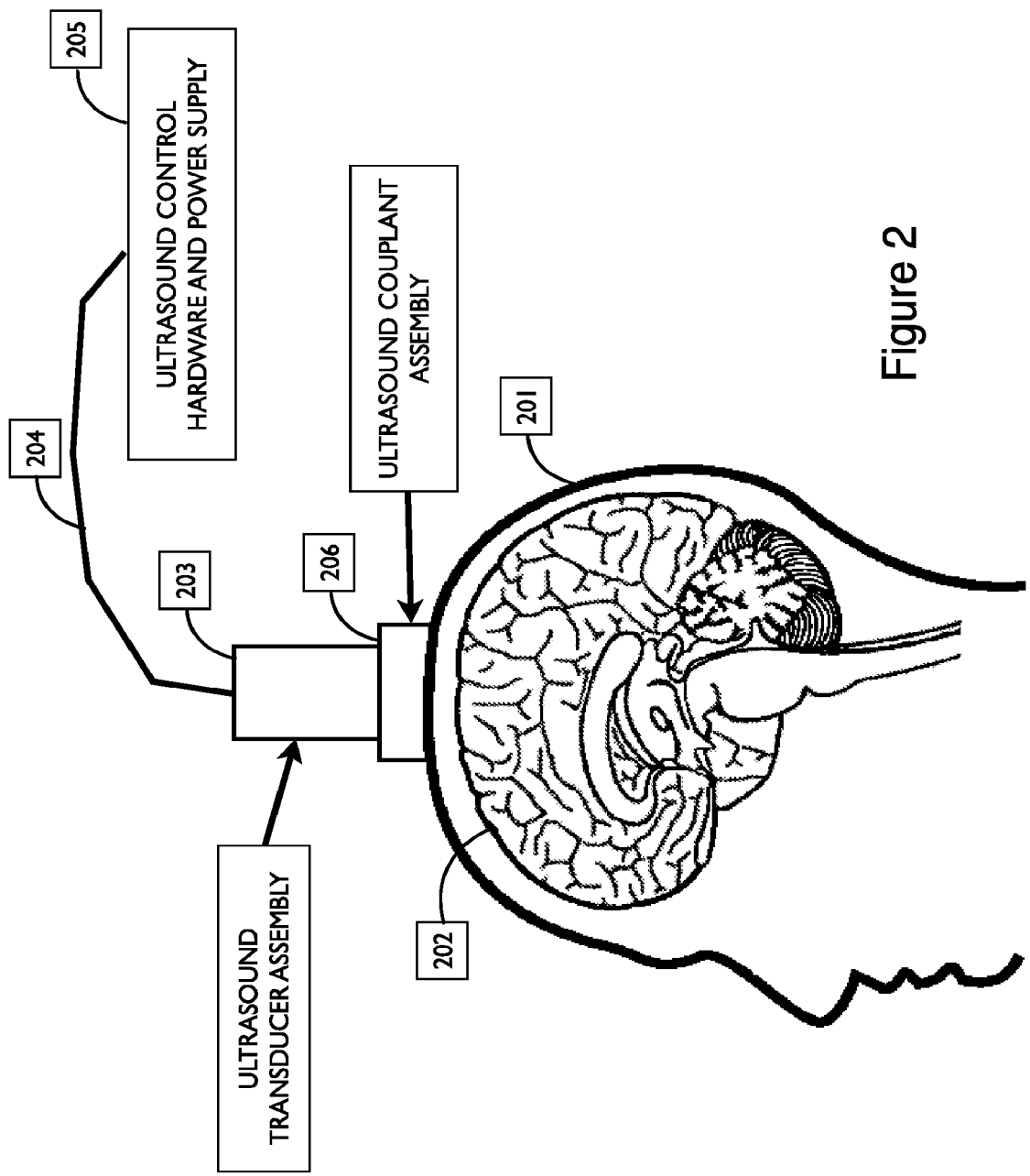
FIG. 2 shows a schematic representation of ultrasound coupling for transcranial ultrasound neuromodulation, in accordance with embodiments.

In an exemplary embodiment of the disclosure, transcranial ultrasound neuromodulation is delivered to a subject (FIG. 2) by a system with core components that include: ultrasound control hardware and power supply 205 attached by cable 204 to at least one ultrasound transducer assembly 203 that is in physical contact with at least one ultrasound couplant assembly 206 used to transmit ultrasound energy through hair, skin, skull, and dura 201 into brain 202. The ultrasound control hardware and power supply are configured to provide appropriate drive signals to one or more ultrasound transducers to generate one or more transcranial ultrasound neuromodulation protocols during a transcranial ultrasound neuromodulation session. Each of the one or more transducer assemblies contains at least one ultrasound transducer configured to generate ultrasound energy with the appropriate one or more dominant acoustic frequencies. Each transducer assembly may incorporate an array of transducers for focusing ultrasound energy. Each transducer assembly may be configured to include connectors, housing, and other electronic and physical components known by one skilled in the art to be required to generate transcranial ultrasound neuromodulation ultrasound protocols.

In an exemplary embodiment of the disclosure, ultrasound energy from a transducer assembly is coupled to the head of the subject through a couplant assembly. In exemplary embodiments, the couplant assembly includes one or more components for ultrasound coupling that is reusable for multiple transcranial ultrasound neuromodulation sessions. As described in detail below, in some embodiments the couplant assembly includes a couplant assembly that is a shaped structure with appropriate acoustic properties (low attenuation of ultrasound for transcranial ultrasound neuromodulation). In some embodiments, a component of the system holds one or more components of the couplant assembly in contact with the transducer and is configured to be removed and replaced by the user. In some embodiments, a mold or shell for a couplant assembly has an attachment portion that fixes to an assembly that includes one or more ultrasound transducers. The attachment portion may include one or more sleeve, bracket, clip, tab, magnet, or other means of attachment known in the art or hereinafter developed. In embodiments of the disclosure, the couplant assembly has a liquid or gel reservoir.

Embodiments of the disclosure in which the couplant assembly is removable from the ultrasound transducer assembly are advantageous, because they permit a user or other individual to replace a couplant assembly. The couplant assembly may require replacement due to physical wear, desiccation, or other degradation. In some embodiments, the couplant assembly can be removed from the ultrasound transducer assembly by hand. In other embodiments, removing the couplant assembly requires one or more tools chosen from the list of allen key, screwdriver, nutdriver, wrench, or other tool known in the art or hereinafter developed.

In various embodiments of the disclosure, the number of times a couplant is designed to be reused is chosen from the list of: once, twice, 3 times, 4 times, 5 times, more than 5 times, more than 10 times, more than 25 times, more than 50 times, more than 100 times, more than 500 times, more than 1000 times, or more than 10,000 times.

Coupling components can be fixed to portions of the system that include the transducer. In accordance with exemplary embodiments, a part of the couplant assembly is configured for attachment to an assembly that includes one or more ultrasound transducers. In some embodiments, a component of the system holds the couplant or couplant assembly in contact with the transducer and is configured to be removed and replaced by the user. In some other embodiments, a mold or shell for a couplant assembly has an attachment portion for fitting to a probe, or an attachment device is embedded, and thereby fixed, in the couplant assembly. In general, any mechanism for attachment is suitable and may include sleeves, brackets, clips, tabs, magnetism, or other means known in the art or hereinafter developed. In some embodiments, one or more clips will hold a mold or shell for a couplant assembly against the assembly that includes one or more ultrasound transducers (e.g. probe housing) and simultaneously compress the seal against the probe housing.

Various materials are advantageous as ultrasound couplants. The materials listed below are particularly advantageous for transcranial ultrasound, including transcranial ultrasound neuromodulation. In some embodiments, multiple components comprise a single couplant assembly.

In some embodiments, the harder or more viscous coupling material of the couplant assembly is a gel. In some embodiments, an additional softer or less viscous material contained in a reservoir of the couplant assembly is also a gel. The one or more gels can be physically crosslinked polymers, chemically crosslinked polymers, or the combination thereof. The gel is optionally filled with small molecules. The examples of small molecules, but not limit to, are water, oil, or salts.

In some embodiments, the gel is prepared from naturally occurred polymers. The examples of naturally occurred polymers include, but are not limited to, collagen, gelatin, hyaluronic acid, fibrin, alginate, agarose, and chitosan. The gel is formed and shaped by addition of crosslinkers. The examples of crosslinker include, but are not limited to, salts, aldehydes, carbodiimides, and epoxides.

In some embodiments, the gel is prepared from synthetic monomers. The synthetic monomers are mono-, di-, tri- or multi-functional acrylates, methacrylates, vinyls, amines, alcohol, carboxylic acids, epoxides, anhydrides, or isocyantes. The synthetic monomers further contain acid, amide, alcohol, ether, PEG, silicon, amine, or hydrophobic functionalities. The gel is formed and shaped via free-radical polymerization process, ring-opening polymerization process, or condensation polymerization process.

In some embodiments, the gel is prepared from synthetic polymers. The synthetic polymers are homo- or co-polymers of acids, amides, alcohols, PEGs, or amine. Examples of synthetic polymers include, but are not limited to, polyvinylalcohols, poly-N-vinyl pyrrolidone, polyacrylamides, polyhydroxyethyl methacrylate, functionalized PEGs, polyethyleneimines. The gel is formed and shaped by addition of crosslinkers. Examples of crosslinkers include, but are not limited to, salts, aldehydes, carbodiimides, anhydrides, isocyanates, amines, and epoxide.

In some embodiments, the shape of the ultrasound coupling portion of the couplant assembly is chosen from the list of: cylindrical, cone-shaped, elliptical, trapezoidal, pyramidal, rectangular, cubic, polygonal, or an irregular three-dimensional shape.

In some embodiments, the couplant assembly further comprises a harder material (stiffener) that imparts improved structural integrity to the couplant assembly. In some embodiments, the harder material completely surrounds the softer material on its sides. In other embodiments, the harder material partially surrounds the softer material on its sides but not on the faces oriented toward the transducer or head. In yet other embodiments, the harder material does not surround the softer material on the faces oriented toward the transducer and/or head. In some embodiments, the rigid material is polycarbonate and/or transparent. In one exemplary embodiment, the softer and more rigid materials are cylindrical and share a common vertical axis.

Heterochromaticity is an advantageous feature of a couplant component for transcranial ultrasound neuromodulation. Heterochromatic materials that emit light or otherwise change the optical properties of one or more components of the couplant are advantageous for indicating when ultrasound is being transmitted. By providing visual feedback showing when ultrasound is transmitted into the head, the recipient of the transcranial ultrasound neuromodulation protocol can determine conclusively when the device is functioning. In some embodiments that incorporate a reservoir of liquid or gel, the liquid or gel contained within the couplant assembly is heterochromatic and the surrounding solid couplant material is transparent but not heterochromatic. In alternative embodiments, an at least one reservoir of liquid or gel contained within the couplant assembly is not heterochromatic but the surrounding solid couplant material is heterochromatic.

Visual feedback about transcranial ultrasound neuromodulation can be beneficial to the recipient or user for several reasons:

(1) By having a conclusive indicator about when ultrasound is transmitted, the user can more effectively maintain safe device function. The user may be less likely to inadvertently have the transcranial ultrasound neuromodulation unit 'on'. The user may also more effectively stay within limits of power and time for ultrasound transmission.

(2) In some embodiments, a device configured to indicate ultrasound transmission visually facilitates targeting of transcranial ultrasound neuromodulation. The timing of when a user or third party administering transcranial ultrasound neuromodulation monitors for a particular induced effect on brain function is made more clear via visual feedback when a heterochromatic component of the couplant changes color.

(3) In some embodiments, the heterochromicity of a couplant material indicates that the couplant needs to be replaced.

(4) In some embodiments, colors or patterns of heterochromacity in a couplant are configured to be visually appealing to the user, another individual administering transcranial ultrasound neuromodulation, or a third party able to observe the administration of transcranial ultrasound neuromodulation. Visually appealing transducer and/or couplant systems are beneficial for marketing purposes and can contribute to positive associations of device use by a user.

Some embodiments include one or more reservoirs of a non-solid material contained within or adjoining a solid component of the couplant assembly. The non-solid material can be liquid (such as water or oil) or a gel. The non-solid material contained within a reservoir is configured to have low impedance mismatch with the harder couplant assembly material for efficient ultrasound energy transfer. In some embodiments, the harder couplant assembly material surrounds and forms the reservoir. In other embodiments, a membrane, housing, or other enclosure is used to form at least one boundary of a reservoir. Couplants that include one or more reservoirs efficiently transmit ultrasound energy. Various embodiments and uses of solid couplant assembly described herein could incorporate one or more fluid-filled or gel-filled reservoir.

In some embodiments, a reservoir is fully contained within the solid components of the couplant. The reservoir sizes, shapes, and positions described herein and shown in drawings are meant to illustrative in accordance with embodiments as described herein. One skilled in the art will recognize that other reservoir designs are consistent with the disclosure as described. In FIGS. 7, 8, 9, 10, 11, and 12, the solid couplant is shown in black and white shapes within the black couplant represent a container 510 that contains a liquid or gel material within a reservoir.

Figure 7:
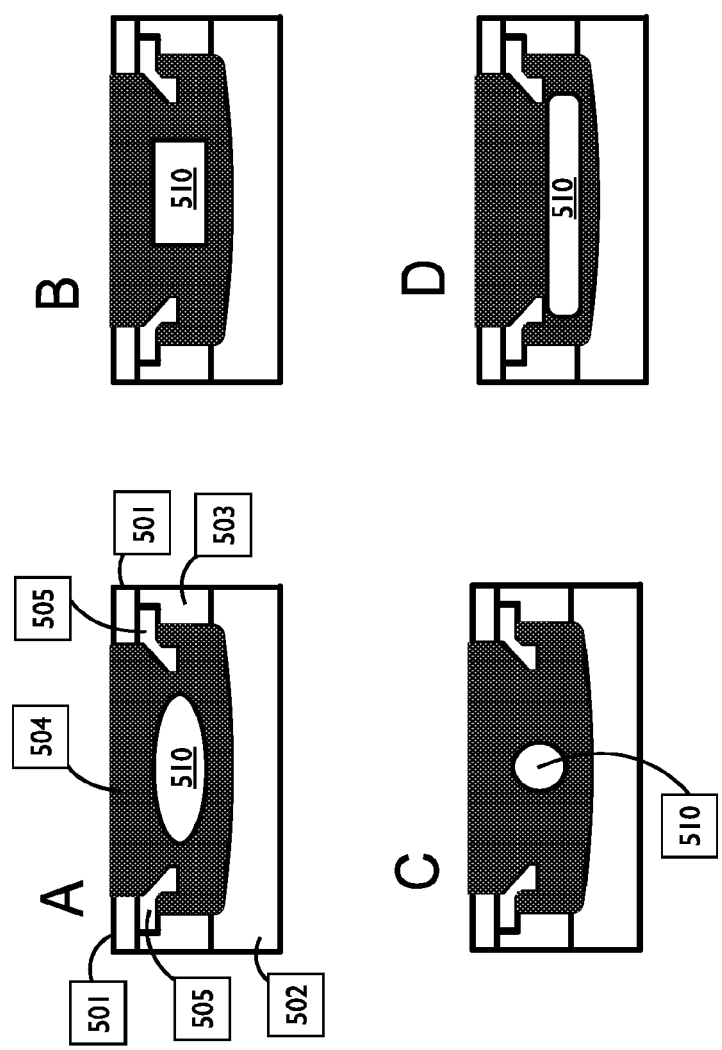
FIG. 7 shows different shapes of fluid-filled reservoirs in a cross-sectional view of a couplant assembly, in accordance with embodiments.

FIG. 7 shows schematic designs (shown in vertical cross section) for couplant assemblies that contain a single reservoir containing a liquid or gel coupling material. In various embodiments, a reservoir can be a regular or irregular shape, including elliptical (panel A), spherical (panel C), rectangular (panel B), or other shapes (panel D). In alternative embodiments, a reservoir may also be trapezoidal, polygonal, fractal, pyramidal, conical, or another regular or irregular shape.

Figure 8:
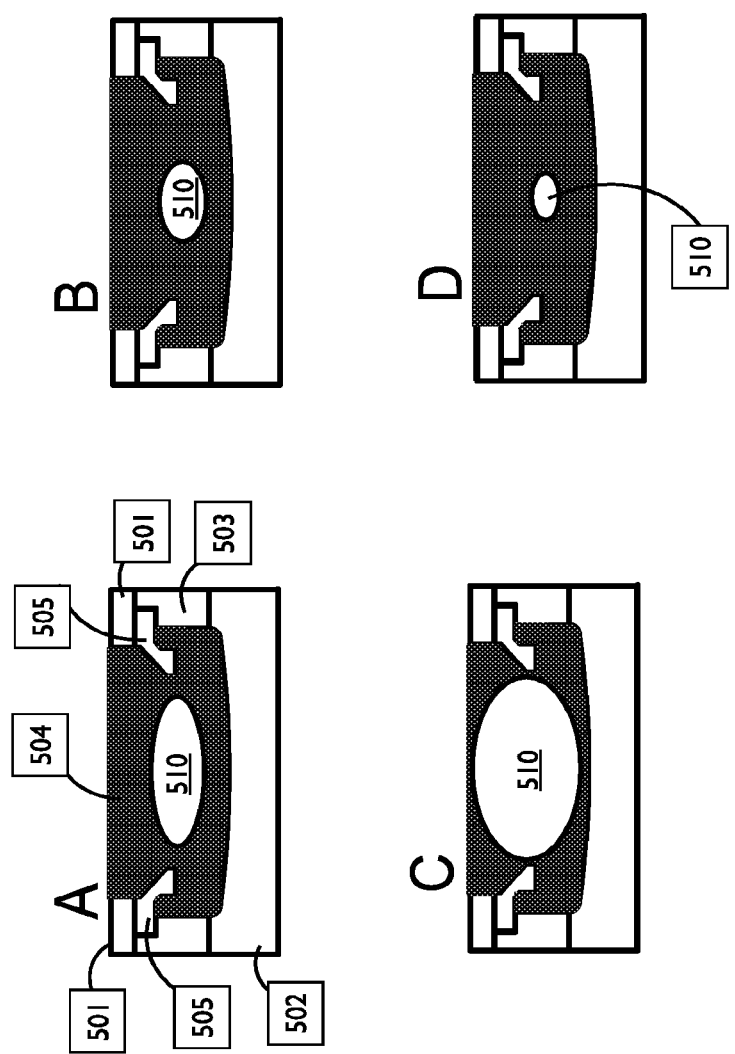
FIG. 8 shows different sizes of fluid-filled reservoirs in a cross-sectional view of a couplant assembly, in accordance with embodiments.

In various embodiments, a reservoir can be different sizes as shown in FIG. 8. The longest dimension of a reservoir may be greater than about 0.1 micron, greater than about 1 micron, greater than about 10 microns, greater than about 100 microns, greater than about 500 microns, greater than about 1 mm, greater than about 2 mm, greater than about 3 mm, greater than about 4 mm, greater than about 5 mm, greater than about 6 mm, greater than about 7 mm, greater than about 8 mm, greater than about 9 mm, greater than about 1 cm, greater than about 1.5 cm, greater than about 2 cm, greater than about 3 cm, greater than about 4 cm, greater than about 5 cm, greater than about 10 cm, greater than about 15 cm, or larger.

Figure 9:
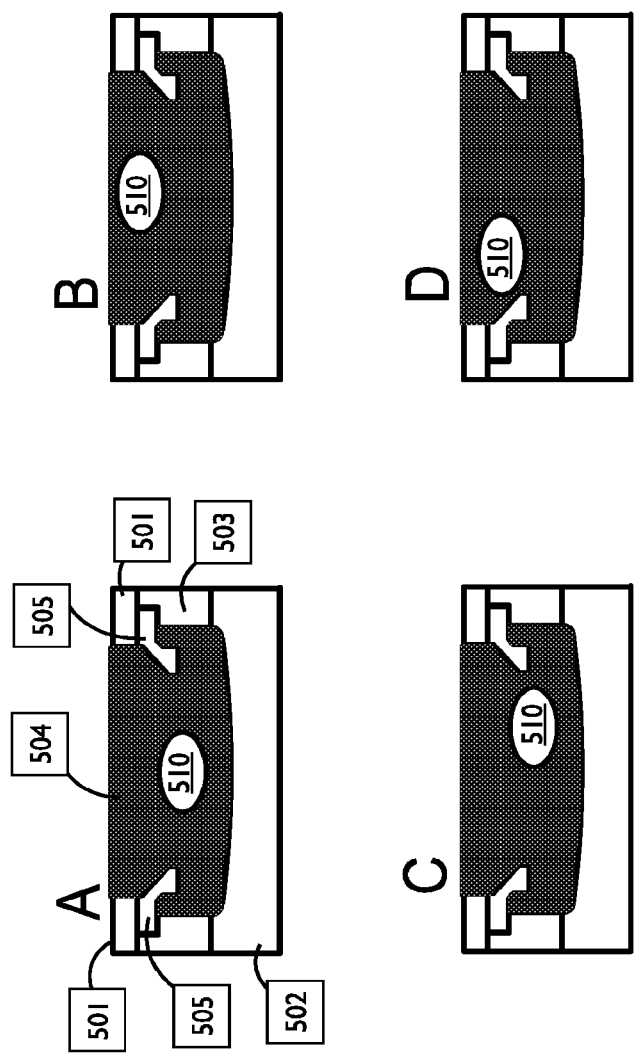
FIG. 9 shows different positions of fluid-filled reservoirs in a cross-sectional view of a couplant assembly, in accordance with embodiments.

In various embodiments, a reservoir can be in various positions within the couplant assembly as shown in FIG. 9, including centered within the depth of the couplant assembly and along the center axis of the Puck (panel A), shifted off the central axis of the couplant assembly (panel C), near the top of the couplant assembly (panel B), or toward a corner of the couplant assembly (panel D). A reservoir may be at a specific position by design or may be generated randomly, stochastically, or pseudo-randomly.

Figure 10:
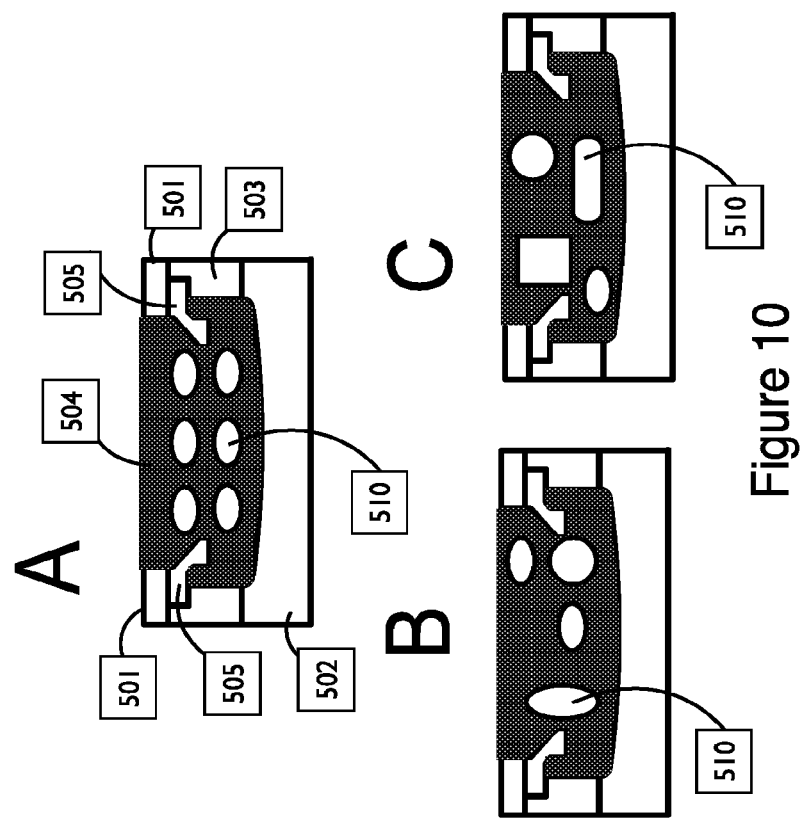
FIG. 10 shows exemplary embodiments of a couplant assembly with multiple reservoirs in a cross-sectional view, in accordance with embodiments.

FIG. 10 shows vertical section schematics of couplant assemblies with multiple reservoirs. In various embodiments, the number of reservoirs in a couplant assembly may be greater than 1 reservoir, greater than 2 reservoirs, greater than 5 reservoirs, greater than 10 reservoirs, greater than 25 reservoirs, greater than 100 reservoirs, greater than 1000 reservoirs, or greater than 10000 reservoirs. The multiple reservoirs contained in a couplant assembly may be similar, identical, or different with respect to shape, size, and position. In some embodiments, a reservoir may be formed of partially overlapping (i.e. continuous) reservoir sections such that the material contained within the reservoir passes freely between the two sections. In FIG. 10, panel A shows six identically-shaped reservoirs arranged in a grid pattern. In FIG. 10, panel B shows four reservoirs, each of which is elliptical but of variable dimensions and positions within the couplant assembly. In FIG. 10, panel C shows four reservoirs that vary in shape, position, and size.

Figure 11:
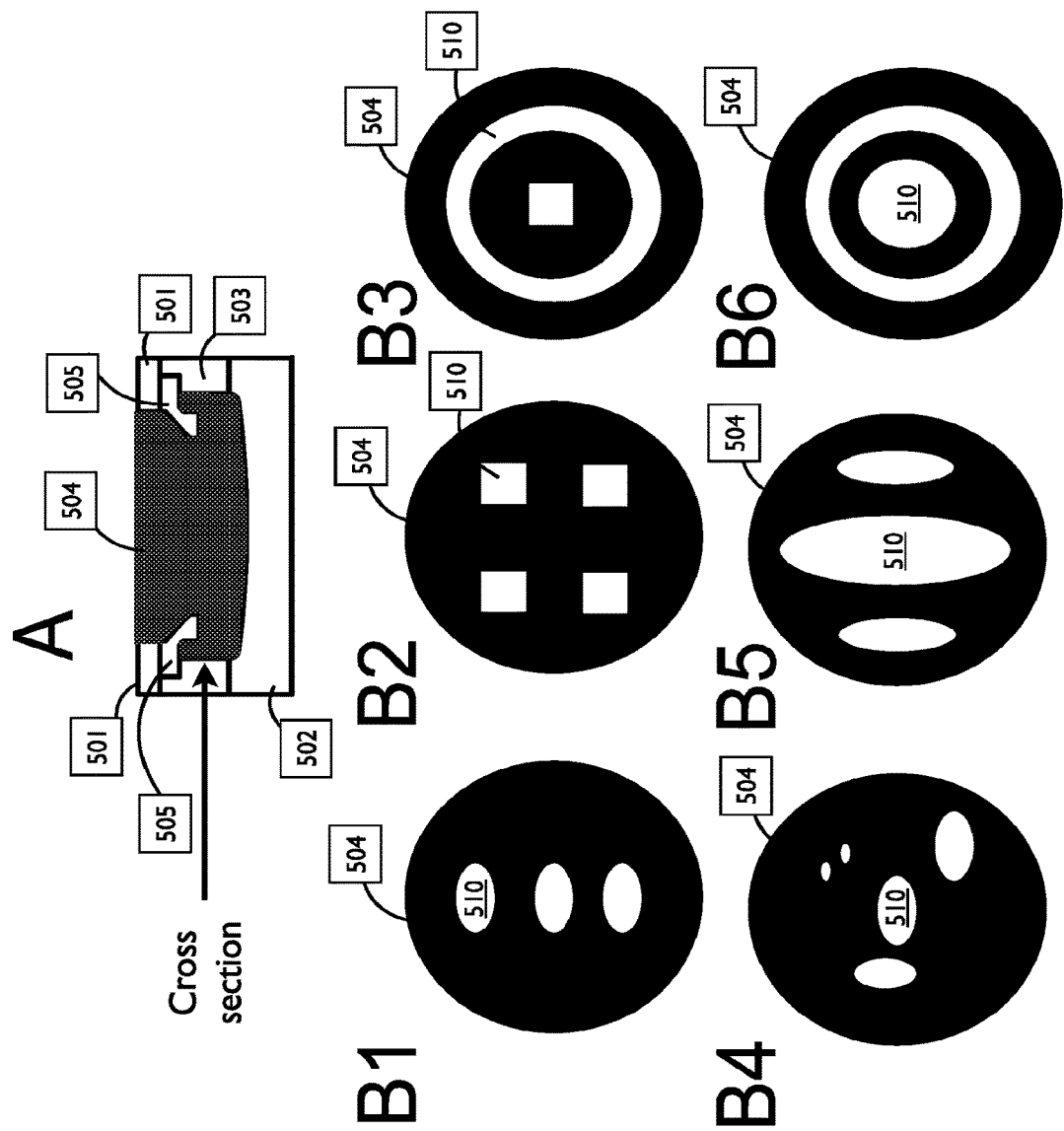
FIG. 11 shows exemplary embodiments of a couplant assembly with multiple reservoirs in a cross-sectional view, in accordance with embodiments.

Panels B1, B2, B3, B4, B5, and B6 of FIG. 11 are transverse section schematics showing embodiments of couplant assemblies with multiple containers defining reservoirs and chambers. Although not shown in the transverse sections of FIG. 11, in various embodiments, the reservoirs may have different heights in the axial dimension up to a height that is less than the height of the couplant assembly. In FIG. 11, panel B1 shows three identically-shaped elliptical reservoirs arranged along a common axis. In FIG. 11, panel B2 shows four identically-shaped reservoirs arranged in a grid pattern. In FIG. 11, panels B3 and B6 show ring-like reservoirs with a second reservoir along the center axis. In FIG. 11, panels B4 and B5 show embodiments with multiple reservoirs of various shapes and positions. The schematic in FIG. 11 panel A indicates the cross section shown in panels B1, B2, B3, B4, B5, and B6.

Figure 12:
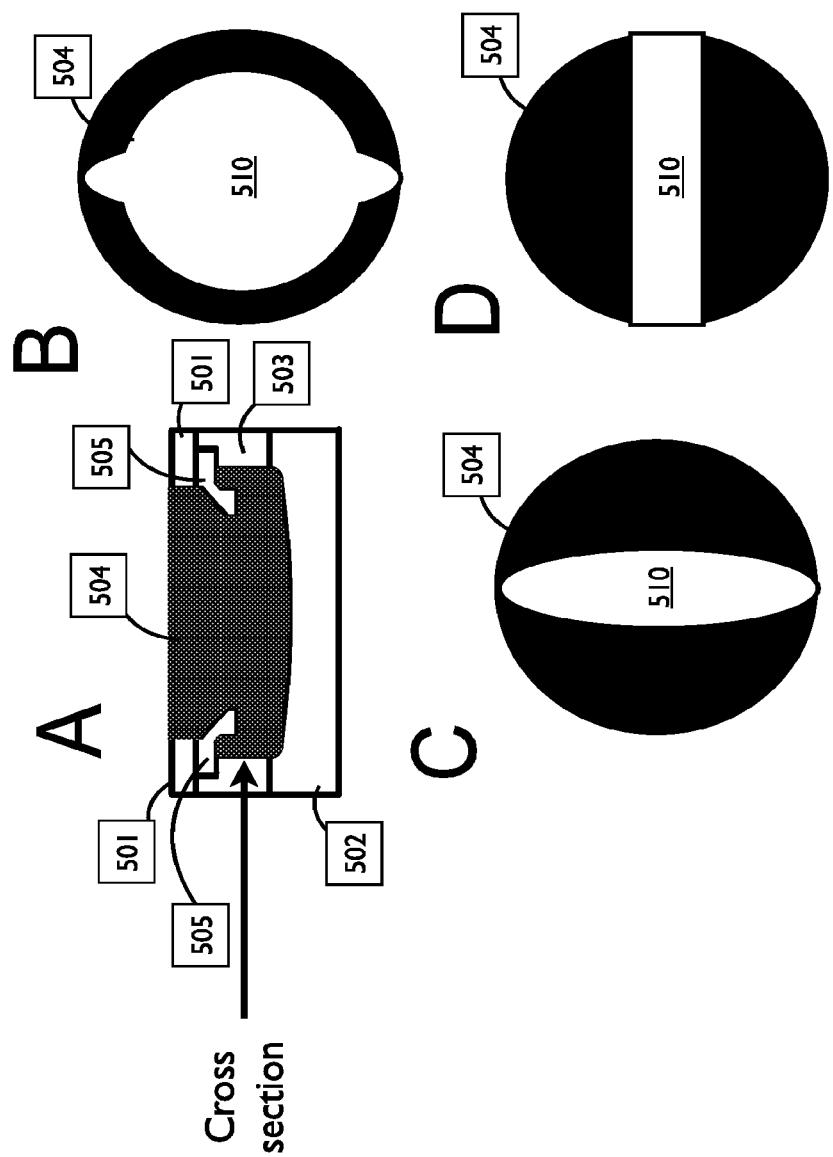
FIG. 12 shows exemplary embodiments of a couplant assembly with a reservoir that spans the full width of the couplant, in accordance with embodiments.
Figure 13:
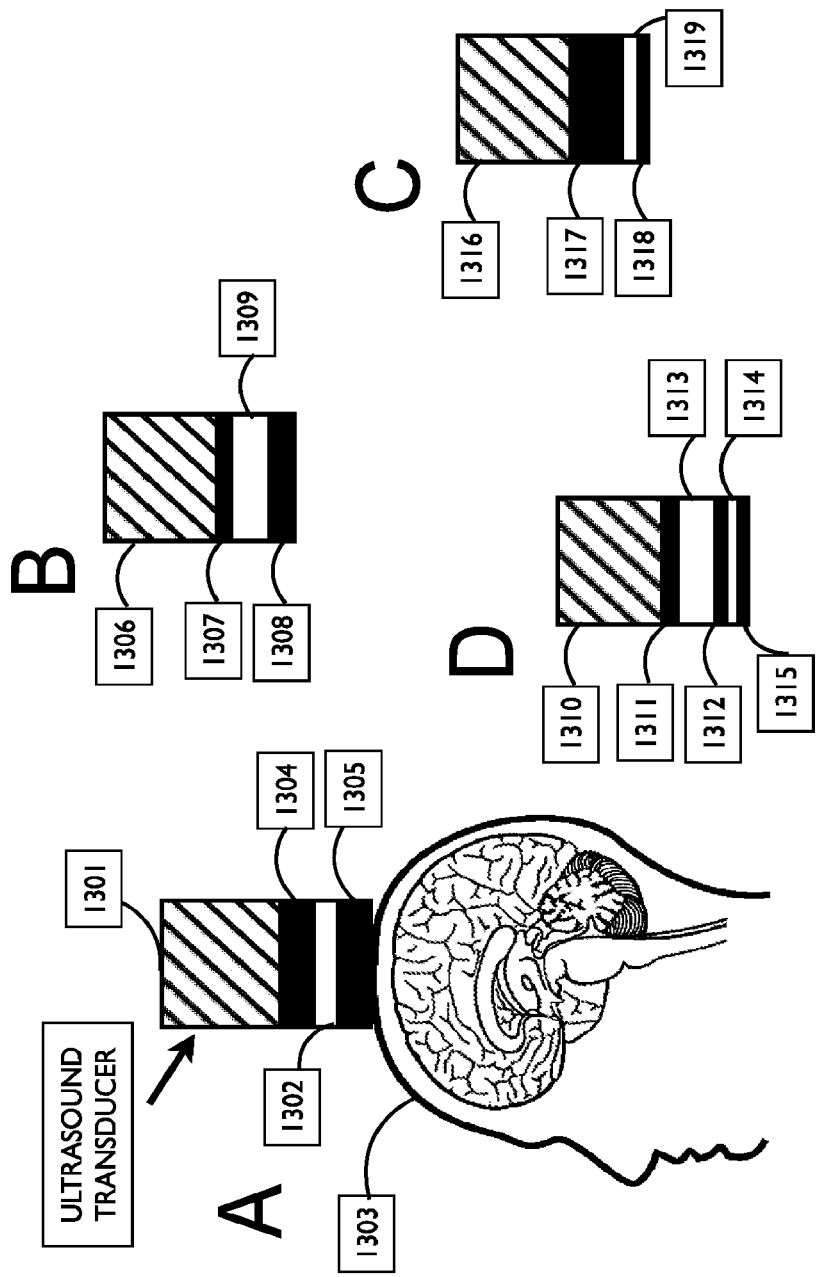
FIG. 13 shows exemplary embodiments of a couplant assembly with one or more reservoirs that span the full width of the couplant, in accordance with embodiments.

As the examples show in FIGS. 12 and 13, in some embodiments of the disclosure, one or more reservoirs spans the full length of at least one dimension of a couplant assembly and incorporates a membrane, housing, shell, or other material at the boundary of the couplant assembly to keep the liquid or gel contained within the reservoir. The schematic in FIG. 12 panel A indicates the cross section shown in panels B, C, and D. In FIG. 12, panel B shows a central reservoir that further includes two side lobes that span the width of the couplant assembly. In FIG. 12, panel C shows a central elliptical reservoir that spans the width of the couplant assembly. In FIG. 12, panel D shows a central rectangular reservoir that spans the width of the couplant assembly.

Figure 14:
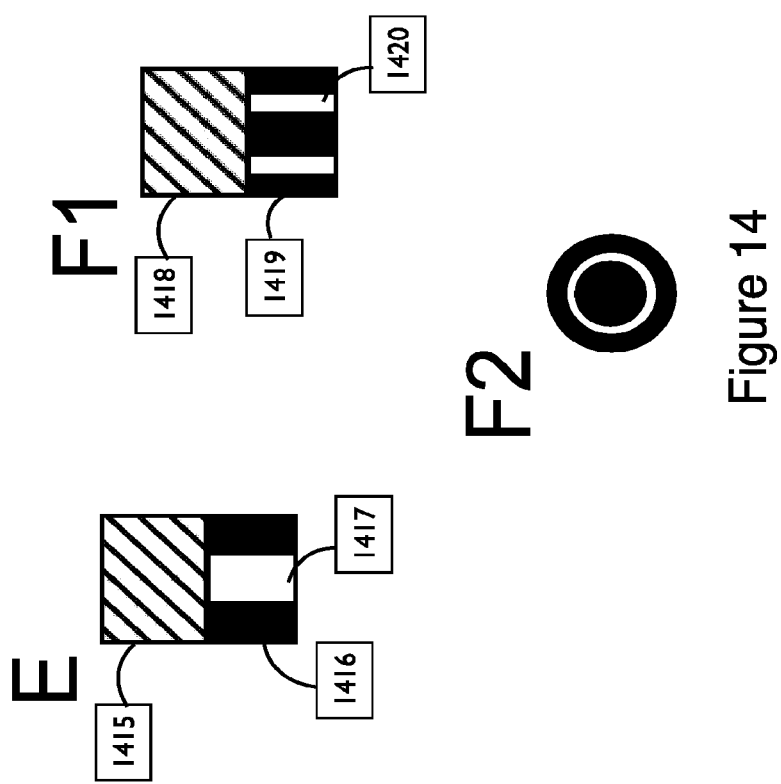
FIG. 14 shows exemplary embodiments of a couplant assembly with one or more reservoirs that span the full height of the couplant, in accordance with embodiments.

In some embodiments, one or more reservoirs comprises a 'slice' or cross section of a couplant assembly. FIG. 13, panels A, B, C, and D show exemplar systems with this property. In FIG. 13, panel A, an assembly is held against or wearably attached to a subject's head that includes ultrasound transducer 1301, solid coupling components 1304 and 1305 physically abutting the transducer, and touching the head of subject 1303 with a reservoir of liquid or non-solid gel 1302 between the solid coupling components. Additional embodiments of transducer (1306, 1316, 1310), solid couplant (1307, 1308, 1317, 1318, 1311, 1312, 1315), and one or more reservoirs (1309, 1319, 1313, 1314) are shown in FIG. 13, panels B, C, and D wherein the number of reservoirs and size of each component vary. In some embodiments, a reservoir spans the full height of a couplant assembly as shown in FIG. 14, panels E, F1, and F2. In FIG. 14, panel E single reservoir 1417 spans the full height of couplant assembly 1416 along the center axis of the couplant assembly. The embodiment of panel E and other couplant designs can be useful for focusing or directing ultrasound energy from ultrasound transducer 1415 if the acoustic impedance of the material comprising the reservoir differs from the acoustic impedance of the surrounding material. FIG. 14, panels F1 and F2 show two views of a ring-shaped reservoir 1420 that spans the height of the surrounding couplant assembly 1419. The embodiment of panels F1 and F2 may also be useful for focusing ultrasound energy from ultrasound transducer 1418. One skilled in the art will recognize that the schematics in FIG. 13 and FIG. 14 intentionally exclude cabling, a power source, and other control hardware required for proper function of an ultrasound transducer system.

The reservoir can be filled or refilled during the manufacturing of the couplant assembly or after the couplant assembly has been manufactured. In an embodiment wherein the reservoir is filled after the couplant assembly has been manufactured, one or more resealable fluidic paths are used for filling a reservoir. In an embodiment wherein the reservoir is filled after the couplant assembly has been manufactured, a needle is used to inject liquid or gel to the reservoirs. In an embodiment wherein the reservoir is filled after the couplant assembly has been manufactured, microfluidic structures are used to fill one or more reservoirs.

Liquid or gel contained in reservoirs or components positioned between solid couplant material can be used to change the flexibility, density, transparency, and other properties of the couplant assembly. In some embodiments, liquid or gel components of a couplant assembly (e.g. reservoirs) may be used as heat sinks to maintain the thermal integrity of a couplant assembly system.

In an embodiments, the material contained in the at least one reservoir comprises water and/or other liquid suitable for coupling ultrasound to the body while also requiring minimal cleanup.

In an embodiment, the material contained in the at least one reservoir comprises a gel.

Another advantageous system for coupling ultrasound energy to the head for transcranial ultrasound neuromodulation comprises a fluid-filled deformable couplant that releases liquid or gel couplant through a semi-permeable or porous membrane portion of the couplant housing when put under pressure. In an embodiment, the liquid is water. In an embodiment, the liquid is an oil. Wang et. al., describe a couplant system with similar features (U.S. Pat. No. 5,494,038 titled "Apparatus for ultrasound testing"), but a system configured for releasing liquid or gel through a permeable, semi-permeable, or porous membrane has not previously been considered for applying ultrasound transcranially such as for transcranial ultrasound neuromodulation.

Figure 15:
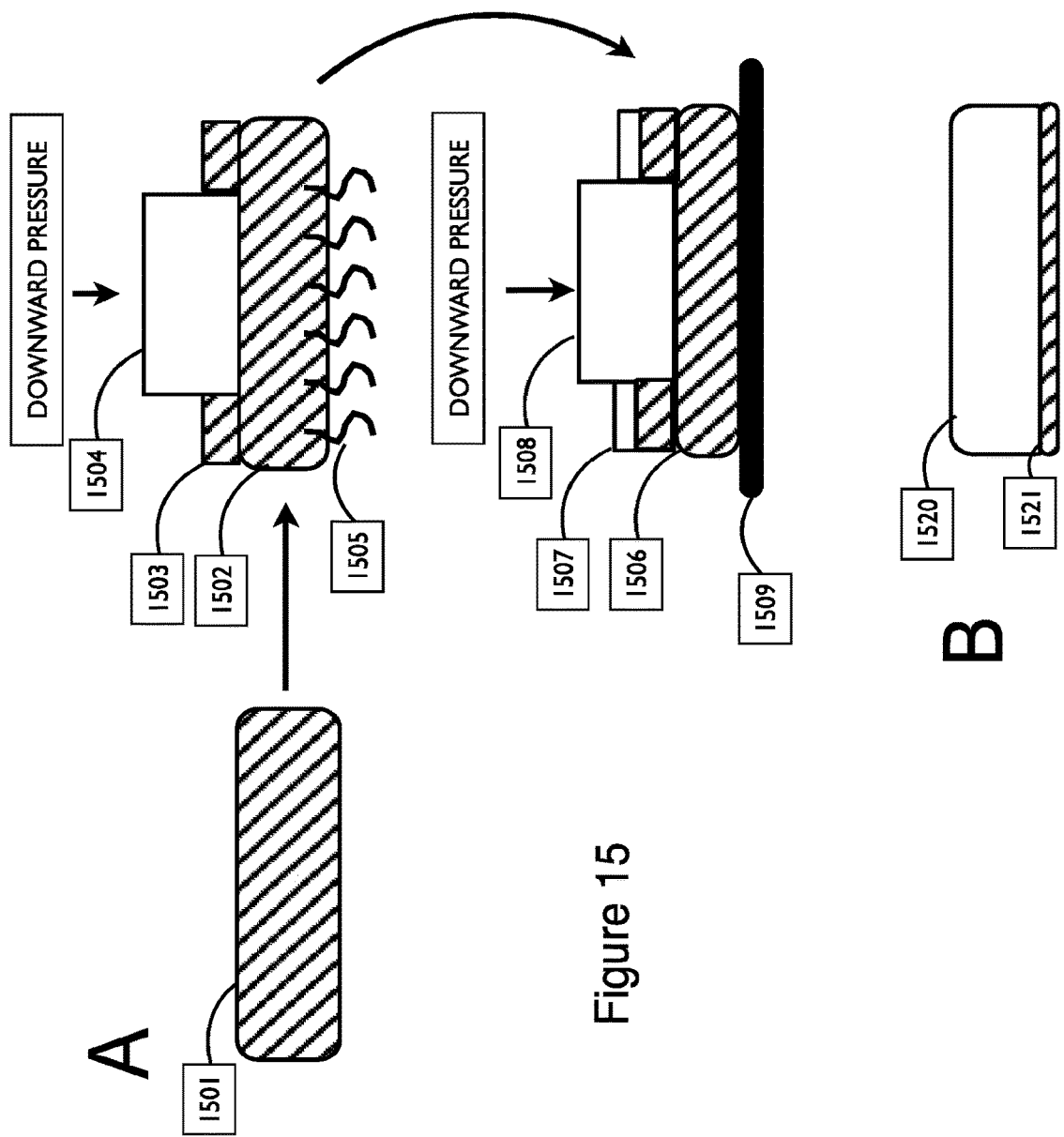
FIG. 15 shows exemplary embodiments of an assembly that releases liquid or gel couplant through a membrane, in accordance with embodiments.

FIG. 15 shows an embodiment of this disclosure. Before use, the couplant 1501 is filled with a liquid or gel couplant material and maintains its shape. In FIG. 15, the couplant material is indicated in the schematics by diagonal hashing. Before a session of transcranial ultrasound, downward pressure is exerted on the couplant 1502 by an ultrasound transducer assembly 1504 either manually or by a mechanical or wearable system. In the embodiment shown in FIG. 15, the transducer assembly has a narrower cross section than the couplant. (In alternate embodiments, the couplant may be narrower or have the same cross section as the transducer or transducer assembly.) The downward pressure causes the couplant to deform, transiently revealing side lobes 1503 and releasing liquid or gel couplant 1505 through a semi-permeable membrane. The released liquid or gel couplant forms a layer 1509 between the couplant assembly 1506 and the body of the subject. After releasing liquid or gel couplant, there may be unfilled portions 1507 of the couplant due to the continued exertion of pressure through the ultrasound transducer assembly 1508. The couplant assembly can be reused in this manner until there is no longer sufficient liquid or gel 1521 in the couplant 1521 to be released and couple ultrasound to a body.

EXAMPLES

Example 1

We assessed several coupling strategies and materials.

First, we tried a thin soft urethane shell filled with ultrasound gel. Though the shell did hold the gel effectively, it did not couple well due to the urethane to skin interface which did not "wet out" very well. Next, we tried molded jello. The jello was put next to the skin. This worked and coupled well, but the jello melted after a determined time due to heating from the skin and transducer. This feature could be positive due to having a disposable tip. Also, if the jello is cool, it may impart comfort to the user.

Compared to these approaches, we found silicone to be an excellent couplant. Silicone Solutions (Twinsburg Ohio) type SS6060 Soft Gel silicone was an appropriate durometer, neither too soft nor too hard. Softer silicone gels such as SS6080 tore too easily, while harder gels (e.g. SS5060) did not conform to a subject for effective coupling. SS6139 Repenetrable Gel was unmoldable and thus not advantageous as a couplant in these studies.

Example 2

Figure 3:
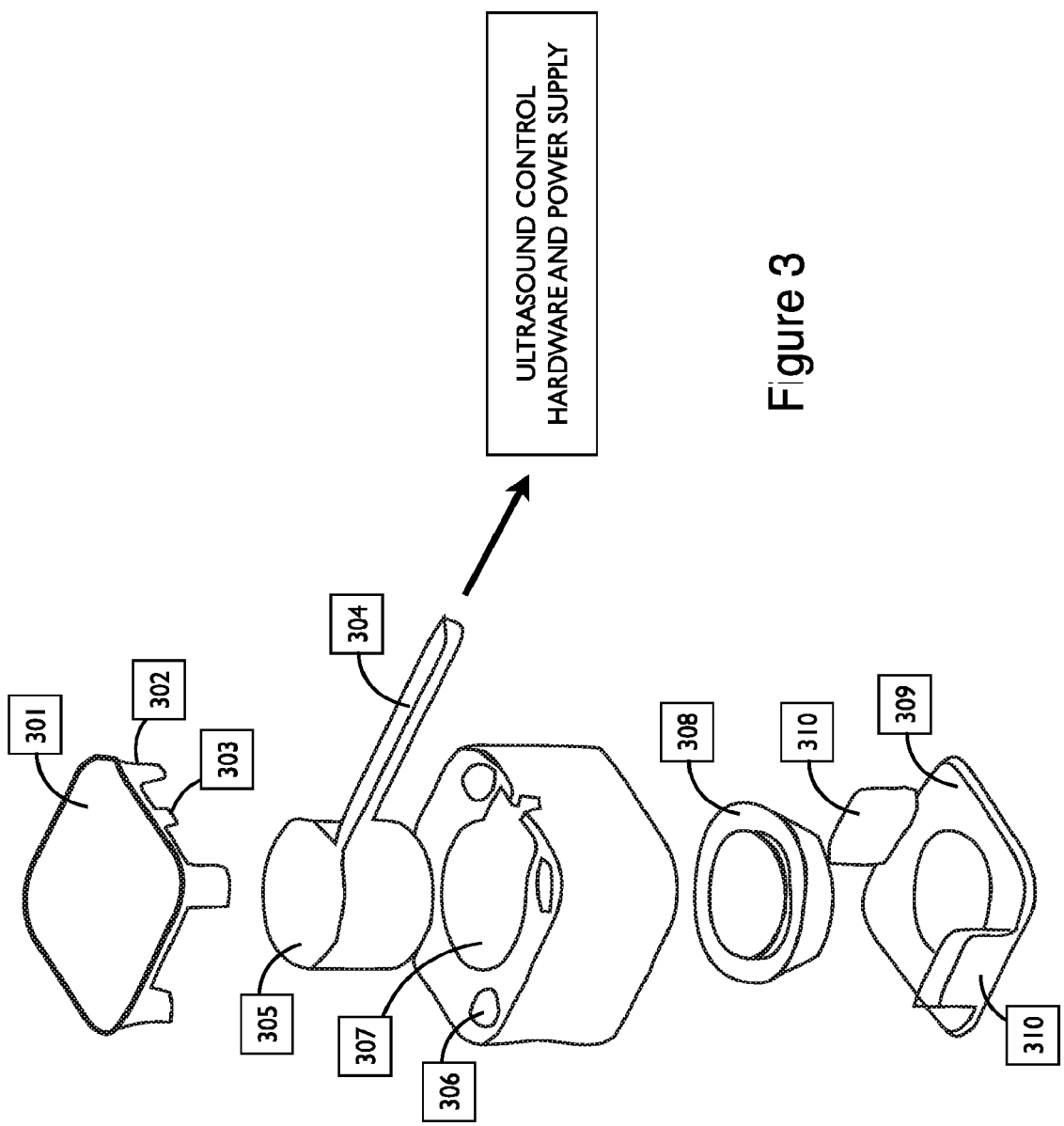
FIG. 3 shows a computer rendering of an exemplary couplant assembly system, in accordance with embodiments.

An exemplary embodiment of a couplant assembly using this silicone is shown in FIG. 3 in an exploded computer rendering of a handheld transducer assembly comprising a solid ultrasound couplant. Top enclosure piece 301 contains corner tabs 302 and alignment tab 303. The top enclosure piece fits above ultrasound transducer 305 that is connected to ultrasound control hardware and power supply by a wire or cable. The top enclosure holds the transducer in place in area 307 by clipping into chassis opening 306. The chassis also incorporates a slot to receive tabs 310 from a lower gel retainer 309 that holds couplant 308 in place.

Example 3

Figure 6:
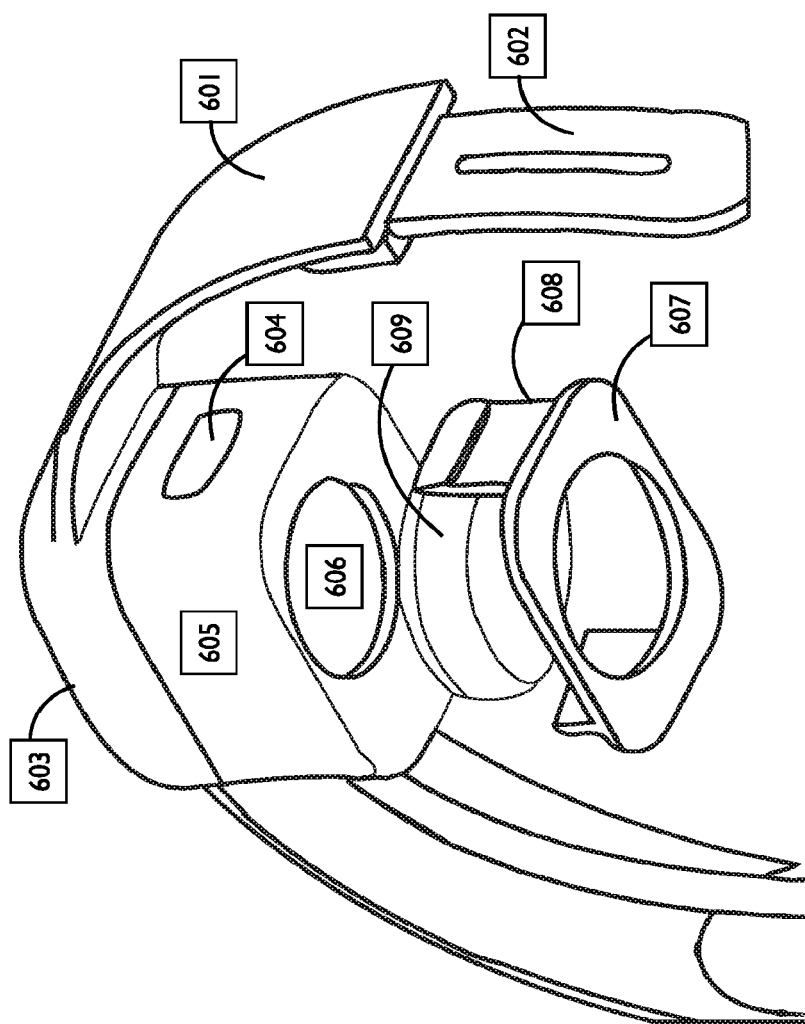
FIG. 6 shows a computer rendering of an ultrasound transducer system and couplant assembly mounted on a wearable headband, in accordance with embodiments.

In another exemplary embodiment, a couplant assembly fits into a housing connected to a headband support for convenient placement on a user's head. In FIG. 6, a schematic shows transducer chassis 603, headband support structure 601, headband adjustment piece 602, clip-in retainer ring 608, couplant 609, and stiffener 607 that provides additional rigidity to the couplant assembly.

Example 4

We tested whether ultrasound energy is efficiently transmitted through silicone.

The transmission of ultrasound energy from a transducer into a calibrated water tank was quantified. For this assessment, the tank contained regular water (as opposed to degassed) and no gels or other agents were used. Spatial peak ultrasound energy was measured with a calibrated ONDA HNR hydrophone with amplifier. A couplant assembly of silicone about 30 mm in diameter and about 2 centimeters tall was used to assess ultrasound transmission. The couplant assembly was made of type SS6060 Soft Gel from Silicone Solutions (Twinsburg, Ohio). For both scenarios (with and without puck), a Blatek 350 kHz flat transducer was used and driven by a 300 mV peak to peak voltage sine wave fed into an E&I 240L RF amp. The transducer was mounted on a motorized 3 axis stage, and the field was scanned first at 3 mm resolution, then at 1 mm resolution, and finally at 0.25 mm resolution successively to identify the location of the spatial peak energy. We then measured the pressure waveform and converted the measured values to $I_{SPPA}$ according to the appropriate calibration curve of the hydrophone. We consistently observed more efficient transmission with the puck (7.09 W/cm$^2$) compared to without the puck (5.57 W/cm$^2$). These results confirm that ultrasound energy can be efficiently transmitted through a shaped couplant assembly of silicone.

Example 5

Figure 4:
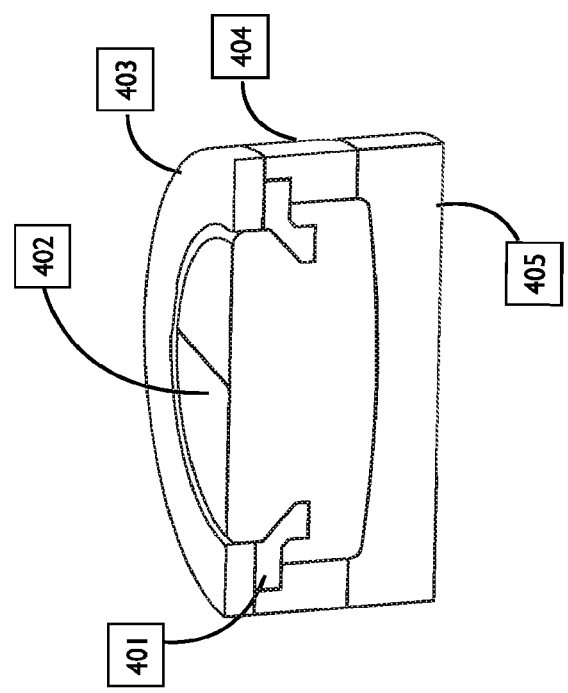
FIG. 4 shows a cross-sectional view of a computer rendering of a solid couplant assembly with stiffener and molds, in accordance with embodiments.
Figure 5:
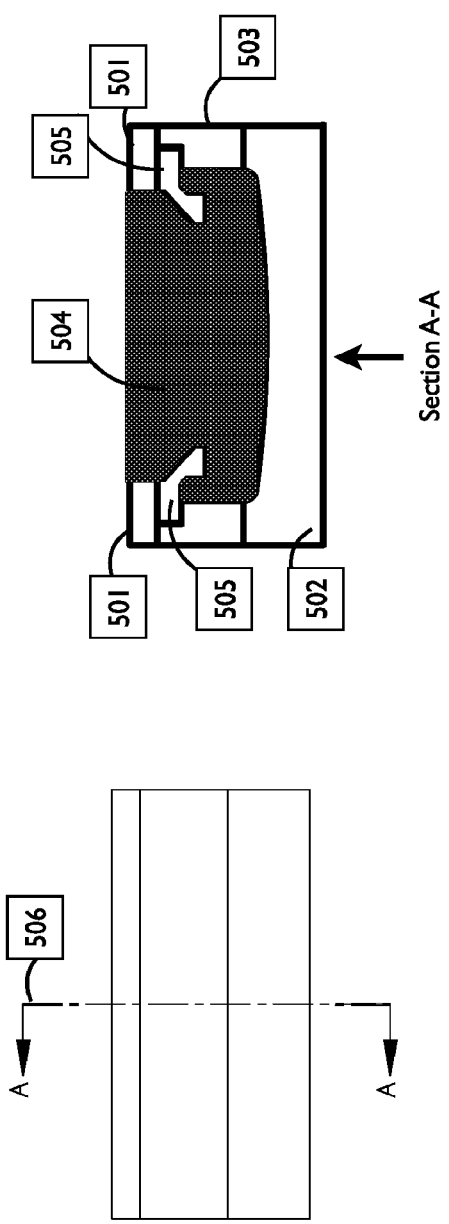
FIG. 5 shows additional cross-sectional views of a computer rendering of a solid couplant assembly with stiffener and molds, in accordance with embodiments.

In one specific embodiment, a couplant assembly is made of Very Soft Gel Silicone Rubber (Product # SS-6080, Silicone Solutions). FIG. 4 shows three-part mold made of polycarbonate 403, 404, 405 used to form a silicone couplant 402 about 30 mm in diameter. To maintain the shape and rigidity of the couplant assembly, stiffener component 401 is optionally used. FIG. 5 shows another schematic view of a 300 mm couplant assembly in cross section at the position of the puck indicated by line A-A at 506. Molded ultrasound couplant 504 is formed from three-part mold 501, 502, 503 and achieves greater rigidity with stiffener components 505. The stiffener, also made of polycarbonate, provides structural support for the couplant assembly. A higher durometer outer skin material imparts rigidity to the inner material that is softer and amenable to reusability as an ultrasound couplant due to minimal residue deposition after adherence to the head. This design significantly improves robustness, while still retaining the advantageous features of the soft inner coupling material that has a lower durometer.

Example 6

In another embodiment of the disclosure, a cylindrical mold is used to create a silicone gel couplant using a slightly stiffer silicone than that used in Example 1 (Silicone Solutions SS-6060 "Soft Gel"). This silicone has advantageous properties as a couplant because it is more durable than the "Super Soft Gel" from example 5 but still "wets out" well.

What is claimed is:

1. A system for coupling ultrasound energy to a subject, the system comprising:
    a couplant assembly having a proximal surface shaped to contact an ultrasound transducer and a distal surface, the couplant assembly including a conformable solid couplant material between the proximal and distal surfaces, wherein the conformable solid couplant material has a Shore D durometer hardness value of less than 60 D, wherein the conformable solid couplant material includes a first surface and a second surface, wherein the proximal surface of the couplant assembly comprises the first surface of the conformable solid couplant material, wherein the distal surface of the couplant assembly comprises the second surface of the conformable solid couplant material, wherein the first surface of the conformable solid couplant material is configured to physically contact the ultrasound transducer, wherein the second surface of the conformable solid couplant material is capable of deflecting at least partially in response to contact with skin or hair of the subject when placed on the subject in order to couple the ultrasound transducer in contact with the proximal surface to the subject, and wherein the conformable solid couplant material fully contains an enclosed reservoir that contains a liquid or gel material, the couplant assembly comprising:
        a housing containing one or more structures of the couplant assembly, the housing comprising:
            a chassis; and
            a retaining ring dimensioned to attach to the chassis to hold the conformable solid couplant material, wherein the housing is configured to hold the proximal surface of the couplant assembly in contact with the ultrasound transducer.

2. The system of claim 1, wherein the couplant assembly comprises a deformable coupling structure that is deformable to conform to a contour of a head of the subject when placed in contact with the head of the subject.

3. The system of claim 1, wherein the conformable solid couplant material comprises a gel.

4. The system of claim 1, wherein the conformable solid couplant material comprises silicone.

5. The system of claim 1, wherein the couplant assembly comprises one or more stiffening assembly components made of a material that is harder than the conformable solid couplant material.

6. The system of claim 1, wherein the couplant assembly is reusable.

7. The system of claim 6, wherein the housing is configured to hold the ultrasound transducer when the couplant assembly is placed on the subject and when the couplant assembly is removed from the subject.

8. The system of claim 7, wherein the couplant assembly is configured to be removeably attached to the ultrasound transducer.

9. The system of claim 1, wherein the distal surface includes a conformable solid couplant material having an internal adhesion strength greater than the adhesion strength between the distal surface and the scalp, skin, or hair of the subject when the distal surface is pressed against the subject.

10. The system of claim 1, wherein the couplant assembly further comprises at least one first material held in contact with at least one second material to provide rigidity to the couplant assembly, a rigidity characteristic of the first material being higher than a rigidity characteristic of the second material.

11. The system of claim 1, wherein the conformable solid couplant material comprises a gel composed of physically crosslinked polymers, chemically crosslinked polymers, or a combination thereof.

12. The system of claim 11 wherein the gel comprises small molecules.

13. The system of claim 1, wherein the conformable solid couplant material comprises a gel prepared from one of i) naturally occurring polymers, (ii) synthetic polymers, and iii) synthetic monomers.

14. The system of claim 1, wherein the conformable solid couplant material comprises a gel prepared from naturally occurring polymers comprising one or more of collagen, gelatin, hyaluronic acid, fibrin, alginate, agarose, and chitosan and wherein the naturally occurring polymers are formed and shaped by addition of crosslinkers to add structural stiffness thereto.

15. The system of claim 1, wherein the conformable solid couplant material comprises a gel prepared from synthetic polymers comprising one or more of homo- or co-polymers of acids, amides, alcohols, PEGs, and amine.

16. The system of claim 1, wherein the conformable solid couplant material comprises a gel prepared from synthetic monomers comprising one or more of mono-, di-, tri- and multi-functional acrylates, methacrylates, vinyls, amines, alcohol, carboxylic acids, epoxides, andydrides, and isocyantes.

17. The system of claim 1, wherein the enclosed reservoir is completely enclosed by the conformable solid couplant material.

* * * * *